United States Patent
Sanghvi et al.

(10) Patent No.: US 12,280,024 B2
(45) Date of Patent: *Apr. 22, 2025

(54) EPINEPHRINE FORMULATIONS

(71) Applicant: Par Pharmaceutical, Inc., Chestnut Ridge, NY (US)

(72) Inventors: Suketu Sanghvi, Kendall Park, NJ (US); Vinayagam Kannan, Morris Plains, NJ (US); Matthew Kenney, New Haven, MI (US)

(73) Assignee: ENDO OPERATIONS LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/477,161

(22) Filed: Sep. 28, 2023

(65) Prior Publication Data

US 2024/0058281 A1 Feb. 22, 2024

Related U.S. Application Data

(63) Continuation of application No. 17/685,090, filed on Mar. 2, 2022, which is a continuation of application
(Continued)

(51) Int. Cl.
*A61K 31/137* (2006.01)
*A61K 9/00* (2006.01)
(Continued)

(52) U.S. Cl.
CPC .......... *A61K 31/137* (2013.01); *A61K 9/0019* (2013.01); *A61K 9/08* (2013.01);
(Continued)

(58) Field of Classification Search
CPC ...... A61K 31/137; A61K 9/0019; A61K 9/08; A61K 47/12; A61K 47/20; A61K 9/0014; A61K 9/0048; A61K 9/0073
See application file for complete search history.

(56) References Cited

U.S. PATENT DOCUMENTS 8,614,210 B2 12/2013 Bhutada et al.
8,628,805 B2 1/2014 Baillie et al.
(Continued)

FOREIGN PATENT DOCUMENTS

EP 2 437 781 A2 4/2012
FR 2 779 061 A1 12/1999
(Continued)

OTHER PUBLICATIONS

Par Pharmaceutical, Inc. "Adrenalin—epinephrine injection." NDA # 204200, marketed from Jul. 1, 2013. https://dailymed.nlm.nih.gov/dailymed/drugInfo.cfm?setid=3b7a4364-668d-4eb2-a20c-04adc35aabe4 (Year: 2013).*
(Continued)

*Primary Examiner* — Benjamin J Packard
*Assistant Examiner* — Lucy M Tien
(74) *Attorney, Agent, or Firm* — ArentFox Schiff LLP & Endo

(57) ABSTRACT

Pharmaceutical compositions comprising epinephrine, methods of administration, and methods of making the same. Compositions may comprise at least one of an active agent, a pH raising agent, an antioxidant, a transition metal complexing agent, a pH lowering agent, a tonicity regulating agent, optionally a preservative, and optionally a solvent.

4 Claims, 6 Drawing Sheets

Related U.S. Application Data

No. 16/817,253, filed on Mar. 12, 2020, now Pat. No. 11,337,938, which is a continuation of application No. 16/258,204, filed on Jan. 25, 2019, now Pat. No. 10,624,864, which is a continuation of application No. 15/969,500, filed on May 2, 2018, now abandoned, which is a continuation of application No. 15/455,991, filed on Mar. 10, 2017, now abandoned, which is a continuation-in-part of application No. 14/863,112, filed on Sep. 23, 2015, now Pat. No. 10,130,592, which is a continuation of application No. 14/818,121, filed on Aug. 4, 2015, now Pat. No. 9,295,657, which is a continuation of application No. 14/657,990, filed on Mar. 13, 2015, now Pat. No. 9,119,876.

(51) Int. Cl.
   *A61K 9/08*    (2006.01)
   *A61K 47/12*   (2006.01)
   *A61K 47/20*   (2006.01)

(52) U.S. Cl.
   CPC .............. *A61K 47/12* (2013.01); *A61K 47/20* (2013.01); *A61K 9/0014* (2013.01); *A61K 9/0048* (2013.01); *A61K 9/0073* (2013.01)

(56) References Cited

U.S. PATENT DOCUMENTS

| | | | |
|---|---|---|---|
| 9,119,876 | B1 | 9/2015 | Kannan et al. |
| 9,283,197 | B1 | 3/2016 | Taneja et al. |
| 9,295,657 | B1 | 3/2016 | Kannan et al. |
| 10,130,592 | B2 | 11/2018 | Kannan et al. |
| 10,624,854 | B2 | 4/2020 | Zhang et al. |
| 2004/0015015 | A1 | 1/2004 | Ammann |
| 2005/0228336 | A1 | 10/2005 | Keusch et al. |
| 2006/0162722 | A1 | 7/2006 | Boehm et al. |
| 2008/0269347 | A1 | 10/2008 | Bruss et al. |
| 2011/0003015 | A1* | 1/2011 | Baillie ............... A61K 45/06 424/711 |
| 2012/0029085 | A1 | 2/2012 | MacKay |
| 2012/0129944 | A1 | 5/2012 | Baillie et al. |
| 2015/0119440 | A1 | 4/2015 | Karolchyk et al. |
| 2015/0246009 | A1 | 9/2015 | Gupta et al. |
| 2017/0165206 | A1 | 6/2017 | Kannan et al. |
| 2017/0189352 | A1 | 7/2017 | Sanghvi et al. |
| 2018/0250245 | A1 | 9/2018 | Sanghvi et al. |
| 2019/0105288 | A1 | 4/2019 | Sanghvi et al. |
| 2019/0151261 | A1 | 5/2019 | Sanghvi et al. |

FOREIGN PATENT DOCUMENTS

| | | |
|---|---|---|
| WO | 93/20168 A1 | 10/1993 |
| WO | 199320168 | 10/1993 |
| WO | 94/08602 A1 | 4/1994 |
| WO | 98/20869 A2 | 5/1998 |
| WO | 00/74772 A1 | 12/2000 |
| WO | 2010/139751 A2 | 12/2010 |
| WO | 2012/094283 A2 | 7/2012 |
| WO | 2014/057365 A1 | 4/2014 |
| WO | 2014/127015 A1 | 8/2014 |
| WO | 2014/140095 A1 | 9/2014 |
| WO | 2014/202088 A1 | 12/2014 |
| WO | 2016/149028 A2 | 9/2016 |

OTHER PUBLICATIONS

"EPIPEN 0.3 mg" In: "Physicians' Desk Reference, 62 edition," Jan. 1, 2008 (3 pages).
Adrenalin Full Prescribing Information, Revised: Dec. 2012, pp. 1-10.
Akers, "Excipient-Drug Interactions in Parenteral Formulations," Journal of Pharmaceutical Sciences, 2002, pp. 2283-2299, vol. 91, No. 11.
Allen, Jr. "The Art, Science, and Technology of Pharmaceutical Compounding," Fourth Edition, 2012, Chapter 2, pp. 19-51 and Chapter 23, pp. 341-257.
Asada et al., "Reactivity of Thiols with Superoxide Radicals," Agricultural and Biological Chemistry, 1976, pp. 1891-1892, vol. 40, No. 9.
Boquet et al., "Injectable Formulations of Poorly Water-Soluble Drugs," Chapter 6, Formulating Poorly Water Soluble Drugs, 2012, pp. 209-242.
Corbett et al., "Intraocular adrenaline maintains mydriasis during cataract surgery," British Journal of Ophthalmology, 1994, pp. 95-98, vol. 78.
David Stepensky et al., Long-Term Stability Study of L-Adrenaline Injections: Kinetics of Sulfonation and Racemization Pathways of Drug Degradation, 93 J. Pharm. Sers . 4, 969 (Apr. 2004).
Grubstein et al., "Stabilization of epinephrine in a local anesthetic injectable solution using reduced levels of sodium metabisulfite and EDTA," Drug Development and Industrial Pharmacy, Jan. 1, 1992, pp. 1549-1566, vol. 18, No. 14.
Kenneth A. Connors et al., Epinephrine in Chemical Stability of Pharmaceuticals: A Handbook for Pharmacists, 2nd ed. (1986).
Ludwig Hoellein and Ulkrize Holzgrabe, Ficts and facts of epinephrine and norepinephrine stability in injectable solutions, 434 Intl J. Pharmaceutics 468 (2012).
Piechocki et al., "Pharmaceutical Photostability and Stabilization Technology," Drugs and the Pharmaceutical Sciences, 2007, pp. 368-369, vol. 163.
Pramanick et al., "Excipient Selection in Parenteral Formulation Development," Pharma Times, Mar. 2013, pp. 65-77, vol. 45, No. 3.
Roscoe et al., "Chelating Agents as Color Stabilizers for Epinephrine Hydrochloride Solutions," Journal of the American Pharmaceutical Association, 1956, pp. 464-470, vol. 45, No. 7.
Schroeter et al., "A Kinetic Study of Acid-Catalyzed Racemization of Epinephrine," Journal of the American Pharmaceutical Association, 1958, pp. 426-430, vol. 47, No. 6.
Suny Oneonta, Advanced Acid-Base Equilibria, Apr. 12, 2011, Chapter 17, Online Textbook, http://www.oneonta.edu/faculty/viningwj/Chem112/Chapter%2017_6_SY.pdf.
Takem Higuchi and Louis C. Schroeter, Kinetics and Mechanism of Formation of Sulfonate from Epinephrine and Bisulfite, 82 J. Am. Chem. soc. 1904 (1960).
Belgaid et al., "Sterilisation of aseptic drug by sterile filtration: Microbiology validation by microbiology challenge test," Journal of Chemical and Pharmaceutical Research, 2014, vol. 6, No. 12, pp. 760-770.
Butler et al., "Removal of dissolved oxygen from water: A comparison of four common techniques," Talanta, Feb. 1994, vol. 41, No. 2, pp. 211-215.
AdrenaClick® (epinephrine injection) Twinject/Adrenaclick, NDA # 020800, approved on May 30, 2003, 35 pages.
American Regent, Inc., "Epinephrine injection, solution," marketed from Mar. 1, 1994, updated Aug. 24, 2011. Retrieved from the Internet <URL:https://dailymed.nlm.nih.gov/dailymed/drugInfo.cfm?setid=daa651e5-40e1-4e87-9775-3f7cc44dff32>, 7 pages.
AUVI-Q® (epinephrine injection), NDA # 201739, approved on Aug. 10, 2012, 24 pages.
EPIPEN® (epinephrine injection) and EPIPEN Jr® (epinephrine injection), NDA #019430, approved on Dec. 22, 1987, 56 pages.
Hospira, Inc., "Epinephrine injection," marked from Sep. 8, 2005, 11 pages.
International Medication Systems, Limited, "Epinephrine injection," marketed from Jul. 1, 2000, updated Apr. 28, 2020. Retrieved from the Internet <URL:https://dailymed.nlm.nih.gov/dailymed/drugInfo.cfm?setid=7b6ffd77-8b25-4ff1-993e-dbfd7e0834cf>, 17 pages.
"Tradename: Empi's Brand of Lidocaine HCI 2% and Epinephrine 1:100,000 Solution for Topical Iontophoretic System for Dermal Iontophoresis with the Dupel® Iontophoresis System," FDA Labeling—Approval Oct. 26, 2004 <URL: https://www.accessdata.fda.gov/drugsatfda_docs/label/2004/21486lbl.pdf> 14 pages.

(56) References Cited

OTHER PUBLICATIONS

"Epinephrine—epinephrine injection, solution—Hospira, Inc." Nov. 2021 <URL: https://dailymed.awsprod.nlm.nih.gov/dailymed/drugInfo.cfm?setid=a01c237d-ae30-4326-9731-fde72505a4a6&audience=consumer>.

"Epinephrine injection, solution," Dailymed, Updated Feb. 4, 2019, <URL: https://dailymed.nlm.nih.gov/dailymed/drugInfo.cfm?setid=2d524e06-907c-400a-e054-00144ff88e88>.

"Marcaine™ With Epinephrine," pp. 1-23, <URL: https://www.accessdata.fda.gov/drugsatfda_docs/label/2020/016964s082lbl.pdf>.

Greer Arthur, "Epinephrine: a short history", Lancet, vol. 3(5), 2015, pp. 350-351.

Highlights of Prescribing Information "AdrenaClick®", Amedra Pharmaceuticals LLC, 2014, 19 pages.

Prescribing Information, "Twinject® 0.3 mg Auto-Injector" and "Twinject® 0.15 mg Auto-Injector", Amedra Pharmaceuticals LLC, Dec. 12, 2012, 19 pages.

\* cited by examiner

FIG 1. Chromatogram of the Impurities Marker Solution using isocratic HILIC with 15% water Solid trace is 280 nm detection; Dashed trace is 346 nm detection. Flow was set at 1.0 mL/min FIG 2: Chromatogram of the Impurities Marker Solution using isocratic HILIC with 18% water. Solid trace is 280 nm detection; Dashed trace is 346 nm detection. Flow was set at 1.0 mL/min FIG 3: Chromatogram of the Impurities Marker Solution using isocratic HILIC with 22% water Solid trace is 280 nm detection; Dashed trace is 346 nm detection. Flow was set at 1.0 mL/min FIG 4: Gradient HILIC separation of individual components of the EpiHILIC Marker Solution
*Labeled peaks are specified degradants, except for AdrS-m and Unk.C-m, which are minor isomers of specified degradants. Peaks marked with a "\*" are unlabeled minor components in the mixture.*

EPINEPHRINE FORMULATIONS

CROSS-REFERENCE TO RELATED APPLICATIONS

This application is a Continuation of U.S. patent application Ser. No. 17/685,090, filed Mar. 2, 2022, which is a Continuation of U.S. patent application Ser. No. 16/817,253, filed Mar. 12, 2020, now U.S. Pat. No. 11,337,938, issued May 24, 2022, which is a Continuation of U.S. patent application Ser. No. 16/258,204, filed Jan. 25, 2019, now U.S. Pat. No. 10,624,864, issued Apr. 21, 2020, which is a Continuation of U.S. patent application Ser. No. 15/969,500, filed May 2, 2018, which is a Continuation of U.S. patent application Ser. No. 15/455,991, filed Mar. 10, 2017, which is a Continuation-in-Part of U.S. patent application Ser. No. 14/863,112, filed Sep. 23, 2015, now U.S. Pat. No. 10,130,592, issued Nov. 20, 2018, which is a Continuation of U.S. patent application Ser. No. 14/818,121, filed Aug. 4, 2015, now U.S. Pat. No. 9,295,657, issued Mar. 29, 2016, which is a Continuation of U.S. patent application Ser. No. 14/657,990, filed Mar. 13, 2015, now U.S. Pat. No. 9,119,876, issued Sep. 1, 2015. The disclosures of the prior applications are hereby incorporated in their entirety by reference.

FIELD OF THE INVENTION

The present invention provides pharmaceutical compositions comprising epinephrine, methods of administration, and methods of making the same.

BACKGROUND

Epinephrine, also known as 4-[(1R)-1-Hydroxy-2-(methylamino)ethyl]-1,2-benzenediol, is the active principle of the adrenal medulla and an endogenous catecholamine which acts directly on both alpha and beta adrenergic receptors. When used in pharmaceutical compositions, epinephrine can act as a non-selective alpha and beta adrenergic agonist and can work rapidly to improve breathing, stimulate the heart, raise dropping blood pressure, reverse hives, and reduce swelling of the face, lips, and throat. Uses for epinephrine include emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. Epinephrine can also be used to increase blood flow in ACLS during CPR, as an adjunct to local anesthesia, and for radiographic uses.

One example of a pharmaceutical composition with epinephrine as an active agent is Adrenalin®, a sympathomimetic agent manufactured and distributed by Par Sterile Products, LLC. Adrenalin® is an epinephrine injection suitable for subcutaneous, intracameral, and intramuscular administration. When diluted, it may also be administered as ophthalmic irrigation or intracameral injection. Adrenalin® is used primarily as an emergency treatment of allergic reactions (Type 1), including anaphylaxis, and for induction and maintenance of mydriasis during intraocular surgery.

Adrenalin® is a clear, colorless solution containing 1 mg/mL epinephrine in a clear glass vial. Adrenalin® is currently available in 1 mL single-dose and 30 mL multi-dose formulations. For the 1 mL product, each 1 mL of Adrenalin® contains 1 mg epinephrine, 9.0 mg sodium chloride, 1.0 mg sodium metabisulfite, hydrochloric acid to adjust pH, and water for injection. For the 30 mL product, each 1 mL of Adrenalin® solution contains 1 mg epinephrine, 9.0 mg sodium chloride, 1.5 mg sodium metabisulfite, hydrochloric acid to adjust pH, 5.4 mg chlorobutanol as a preservative and water for injection. The pH range of Adrenalin® is 2.2-5.0.

Adrenalin® 1 mL is FDA approved for an 18 month shelf life. The Adrenalin® 30 mL product is approved for an even shorter shelf life of 14 months. Shelf life is limited by the formation of degradants, which mainly comprise epinephrine sulfonic acid (ESA) and D-epinephrine, an enantiomer of L-epinephrine that has insignificant therapeutic activity. The currently approved Adrenalin® 1 mL product has a total impurity limit of <20%. Adrenalin® 1 mL has a concentration limit of <13.5% ESA and <9.5% D-epinephrine. The currently approved Adrenalin® 30 mL product has a total impurity limit of <20%. Adrenalin® 30 mL has a concentration limit of <14.5% ESA and <9.5% D-epinephrine.

There is currently a need in the art for improved epinephrine-containing pharmaceuticals. It is an object of the present invention to provide an epinephrine-containing pharmaceutical composition that addresses some of the limitations of present formulations.

SUMMARY OF THE INVENTION

The present invention provides a pharmaceutical composition comprising epinephrine. The composition may be useful for emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. The composition may also be used to increase blood flow in ACLS during CPR, as an adjunct to local anesthesia, and for radiographic uses. The composition may be administrable via subcutaneous, intracameral, intravenous, and intramuscular injection, infusion, intra-arterial administration, intracardiac injection, endotracheal administration, intraosseous administration, oral inhalation, topical administration, and as ophthalmic irrigation.

The present invention also provides for a composition comprising at least one of an active agent, a pH raising agent, an antioxidant, a transition metal complexing agent, a pH lowering agent, a tonicity regulating agent, optionally a preservative, and optionally a solvent.

The present invention also provides for compositions with low levels of D-epinephrine.

The present invention also provides for compositions with low levels of epinephrine sulfonic acid (ESA).

The present invention also provides for compositions with low levels of oxidative degradants.

The present invention also provides for compositions with low levels of total impurities.

The present invention also provides for compositions comprising a pH raising agent.

The present invention also provides for compositions comprising an antioxidant.

The present invention also provides for compositions that may resist significant pH change over shelf life.

The present invention also provides for a method of making such compositions.

The present invention also provides for a method of treating a medical condition comprising administering to a subject in need thereof a composition of the present invention.

DETAILED DESCRIPTION OF THE INVENTION

Figure 1:
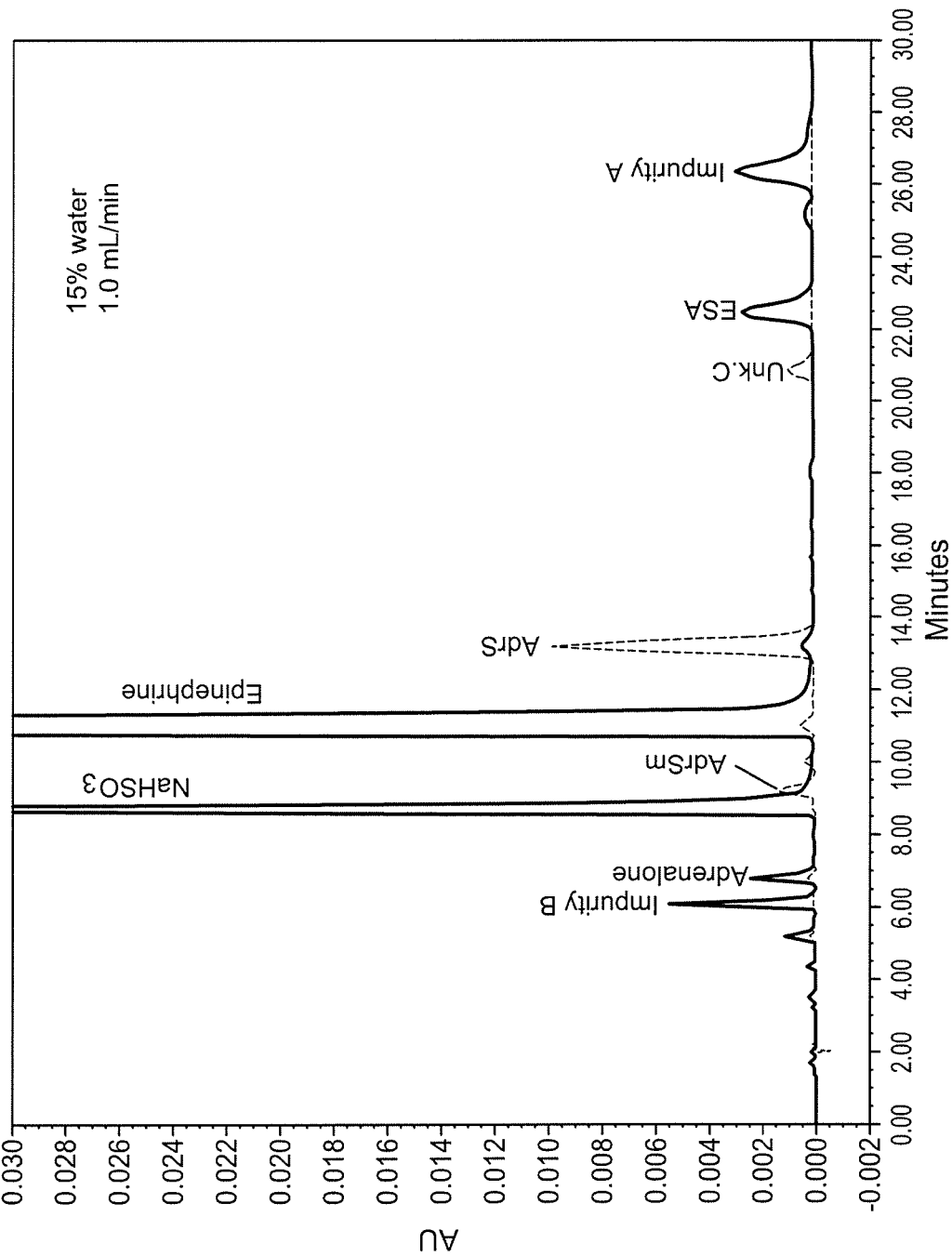
FIG. 1 is a chromatogram of the Impurities Marker Solution using isocratic HILIC with 15% water.

The present invention provides a pharmaceutical composition comprising epinephrine. The composition may be useful for emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. The composition may also be used to increase blood flow in ACLS during CPR, as an adjunct to local anesthesia, and for radiographic uses. The composition may be administrable via subcutaneous, intracameral, intravenous, and intramuscular injection, infusion, intra-arterial administration, intracardiac injection, endotracheal administration, intraosseous administration, oral inhalation, topical administration, and as ophthalmic irrigation.

The present invention provides for a composition comprising at least one of an active agent, a pH raising agent, an antioxidant, a transition metal complexing agent, a pH lowering agent, a tonicity regulating agent, optionally a preservative, and optionally a solvent.

In some preferred embodiments, the composition may comprise an active agent, a pH raising agent, an antioxidant, a pH lowering agent, and a tonicity regulating agent. In some preferred embodiments, the composition may comprise an active agent, an antioxidant, and a tonicity regulating agent. In some preferred embodiments, the composition may comprise an active agent, a transition metal complexing agent, a pH raising agent, a pH lowering agent, and a tonicity regulating agent. In some preferred embodiments, the composition may comprise an active agent, a transition metal complexing agent, an antioxidant, and a tonicity regulating agent. In some preferred embodiments, the composition may comprise an active agent, a pH raising agent, a pH lowering agent, and a tonicity regulating agent. One of ordinary skill will appreciate that the combination of components in the composition may be varied in order to obtain compositions with desired properties.

In some embodiments, the active agent comprises epinephrine and/or salts thereof. Examples of epinephrine salts include, but are not limited to, acetate, carbonate, citrate, hydrochloride, hydrocyanide, hydrofluoride, nitrate, nitrite, phosphate, and sulfate salts. Preferably, the salt is a hydrochloride salt.

In some embodiments, the active agent is present at a concentration sufficient for any of the uses described herein. In some embodiments, the active agent is present at a concentration of about 0.01 to 2 mg/mL, preferably about 0.01 to 1 mg/mL, more preferably about 0.01 to 0.5 mg/mL, more preferably about 0.01 to 0.3 mg/mL, and most preferably 0.01 to 0.2 mg/mL. Alternatively, the active agent is present at a concentration of about 0.1 to 2 mg/mL, preferably about 0.5 to 1.5 mg/mL, more preferably about 0.75 to 1.25 mg/mL, and most preferably about 1 mg/mL. In some embodiments, the active agent is present at a concentration of 0.114 mg/mL or 1.14 mg/mL.

The present invention provides for a composition that may comprise at least one pH raising agent in an amount that raises the pH of the composition. In some embodiments, the pH raising agent comprises a buffer system. The term "buffer system" refers to a component present in a composition or solution which may provide a resistance to significant change in pH caused by a strong acid or base. A buffer system may comprise a single agent or more than one agent, such as a weak acid and its conjugate base. A buffer system may provide a resistance to a significant pH change by interacting with a strong acid or strong base in a composition or solution, thereby at least partially preventing the pH of the composition or solution from changing significantly.

Generally, a buffer system has one or more buffer ranges wherein the buffer system has the ability to provide resistance to significant pH change. When a composition or solution comprising the buffer system has a pH inside the buffer system's buffer range, the pH of the composition or solution will not change significantly with the addition of equimolar amounts of a strong acid or strong base.

The buffer range of a buffer system is related to the acid dissociation constant ($K_a$) of one or more weak acids comprised by the buffer system. The term "acid dissociation constant" refers to the equilibrium constant of a dissociation reaction of an acid. The midpoint of a buffer range for a buffer system is generally about the logarithmic measure of the acid dissociation constant (i.e., the $pK_a$, equal to $-\log_{10}K_a$) of a weak acid comprised by the buffer system.

In some embodiments, the pH raising agent may comprise one or more $pK_a$ values. In some embodiments, the pH raising agent may comprise a $pK_a$ value that is within +/−1 unit of the initial pH of the pharmaceutical composition in the form of a solution without the pH raising agent. In some embodiments, the pH raising agent may have a $pK_a$ value within the range of about 2 to 5, preferably within the range of about 3 to 4.5, more preferably within the range of about 3.5 to 4.5, and most preferably about 4.

In some embodiments, the pH raising agent may have a buffer range from a pH of about 2 to 5, preferably from a pH of about 3 to 4.5, and most preferably from a pH of about 3.5 to 4.5.

In some embodiments, the pH raising agent may provide a resistance to a significant change in pH that other components of the composition may otherwise cause in the absence of the pH raising agent. In some preferred embodiments, the pH raising agent may provide a resistance to the composition's pH being significantly lowered by degradants and/or reaction products of other components of the composition. For example, the pH raising agent may help resist an increase in acidity associated with the chemical reaction of an antioxidant.

In some embodiments, the pH raising agent may be present at a concentration in the range of about 0.1 and 4 mg/mL, preferably in the range of about 1 and 3 mg/mL, preferably in the range of about 1.5 and 2.5 mg/mL, and most preferably about 2.25 mg/mL. In some embodiments, the pH raising agent may be present at a concentration that provides a resistance to a significant change in the composition's pH despite physical and chemical changes of the composition after a certain period of shelf life.

In some embodiments, the pH raising agent is selected such that the degradation of other components of the composition is slowed or reduced, as compared to a composition in which the pH raising agent is not present. For example, the pH raising agent may at least in part help prevent significant degradation of an antioxidant after a certain period of shelf life.

In some embodiments, the pH raising agent is selected such that less antioxidant is present, as compared to a composition in which the pH raising agent is not present.

For example, the pH raising agent may be selected such that the concentration of antioxidant necessary for preventing and/or inhibiting the formation of unacceptable amounts of oxidative degradants in the composition after a certain period of shelf life is lowered by in the range of about 10% to 90%, preferably in the range of about 20% to 80%, more preferably in the range of about 25% and 75%, more preferably in the range of about 30% and 70%, and most preferably in the range of about 40% and 60%, as compared to a composition in which the pH raising agent is not present.

In some embodiments, the pH raising agent and pH raising agent concentration is such that compositions conform to the limit on total acidity imposed by the United States Pharmacopeia (USP) 37-NF 32, S2, monograph, effective from Dec. 1, 2014. For example, the pH raising agent may be selected such that when 5.0 mL of the composition is titrated with 0.01 N NaOH, the total amount of titrant necessary to reach a pH of 7.4 is no more than 25 mL. The pH raising agent may be selected such that the composition has a titratable acid concentration of in the range of about 30 to 70 mM, preferably in the range of about 40 and 60 mM, and most preferably about 50 mM.

In some embodiments, the pH raising agent is suitable for subcutaneous, intracameral, intramuscular, parenteral, and/or ophthalmic use.

Preferably, pH raising agents comprise the acids or salt forms of one or more of lactate, tartarate, glutamate, malate, citrate, gluconate, benzoate, succinate, acetate, glycine, and aspartate, as well as lithium hydroxide, sodium hydroxide, potassium hydroxide, rubidium hydroxide, cesium hydroxide, calcium hydroxide, strontium hydroxide, and barium hydroxide. Preferably, the pH raising agent comprises at least one of tartaric acid and sodium hydroxide, and more preferably both of these compounds.

The present invention provides for a composition that may comprise at least one antioxidant. The term "antioxidant" refers to a component in a composition that may prevent and/or inhibit the formation of unacceptable amounts of oxidative degradants in the composition after a certain period of shelf life. In some embodiments, the antioxidant may react with oxygen that might otherwise compromise the composition by producing impurities in the composition. Oxygen may originate from the composition's environment or the composition itself. For example, oxygen may originate from residual oxygen present in the headspace of vials containing the composition.

In some embodiments, the oxidative degradants comprise one or more of adrenalone, adrenochrome, adrenolutin, adrenochrome sulfonate, and melanins.

In some embodiments, the antioxidant may limit the formation of oxidative degradants in the composition to less than about 1%, preferably less than about 0.5%, more preferably less than about 0.1%, more preferably less than about 0.05%, more preferably less than about 0.04%, more preferably less than about 0.03%, more preferably less than about 0.02%, more preferably less than about 0.01%, most preferably less than about 0.009%, after a certain period of shelf life.

In some embodiments, the antioxidant may inhibit and/or prevent the composition from undergoing unacceptable physical changes. In some embodiments, the antioxidant may inhibit and/or prevent unacceptable composition color change. In some embodiments, the antioxidant may inhibit and/or prevent unacceptable amounts of insoluble particles.

In some embodiments, the antioxidant may inhibit and/or prevent the composition from undergoing unacceptable color changes that may be detected by visually examining a portion of a sample in a clear, glass test tube against a white background. In some embodiments, the antioxidant may inhibit and/or prevent the composition from undergoing unacceptable color changes that may be detected by comparing the absorbance of a sample of the composition in a 1-cm quartz cell using a spectrophotometer set at 460 nm with a 0.0004 N Iodine Standard Solution that is prepared with water and iodine. In some embodiments, the antioxidant may inhibit and/or prevent the composition from containing unacceptable amounts of particulate matter that may be detected by the methods described in USP <788>and/or USP <789>, the disclosures of which are included herein by reference.

In some embodiments, the antioxidant may be present at the lowest concentration that will inhibit and/or prevent the composition from undergoing unacceptable physical changes. In some embodiments, the antioxidant may be present at the lowest concentration that will inhibit and/or prevent unacceptable oxidation of components of the composition.

In some embodiments, the antioxidant may be present at a concentration of in the range of about 0.1 to 3.0 mg/mL, preferably in the range of about 0.3 to 2.7 mg/mL, more preferably in the range of about 0.5 to 2.5 mg/mL, more preferably in the range of about 0.7 to 2.3 mg/mL, more preferably in the range of about 1.0 and 2.0 mg/mL, more preferably in the range of about 1.3 and 1.7 mg/mL, most preferably about 1.5 mg/mL. In some embodiments, the antioxidant may be present at a concentration of in the range of about 0.1 to 1.1 mg/mL, preferably in the range of about 0.1 to 0.9 mg/mL, more preferably in the range of about 0.2 and 0.8 mg/mL, more preferably in the range of about 0.3 and 0.7 mg/mL, more preferably in the range of about 0.4 and 0.6 mg/mL, and most preferably about 0.4 to 0.5 mg/mL.

In some embodiments, the concentration of antioxidant in the composition after a certain period of shelf life may be affected by other components of the composition that reduce and/or slow the rate of antioxidant degradation.

In some embodiments, other components of the composition may reduce and/or slow oxidation of the antioxidant after a certain period of shelf life. For example, when the antioxidant is sodium bisulfite, sodium metabisulfite, or another sulfite, other components of the composition may reduce and/or slow the oxidation of bisulfite to bisulfate.

In some embodiments, other components of the composition may reduce and/or slow protonation and/or desolvation reactions involving the antioxidant over a certain period of shelf life. For example, when the antioxidant is sodium bisulfite, sodium metabisulfite, or another sulfite, other components of the composition may reduce and/or slow the conversion to sulfur dioxide.

In some embodiments, other components of the composition may reduce and/or slow the degradation of antioxidant by raising the composition's initial pH and/or the pH of the composition after a certain period of shelf life, as compared to a composition in which the other components are not present. In some embodiments, the pH raising agent may, at least in part, lead to a reduction in the total degradation and/or degradation rate of antioxidant in the composition after a certain period of shelf life.

In some embodiments, other components are present in the composition at a concentration that reduces the concentration of antioxidant degradation products present in the composition after a certain period of shelf life. In some embodiments, other components are present in the composition at a concentration that increases the concentration of the antioxidant present in the composition after a certain period of shelf life, as compared to a composition in which the other components are not present. In some embodiments, the reduction and/or inhibition of unacceptable antioxidant degradation after a certain period of shelf life may reduce the initial concentration of antioxidant necessary to inhibit and/or prevent the composition from undergoing unacceptable physical changes after a certain period of shelf life. In some embodiments, less than about 90% of the initial amount of antioxidant is degraded after a certain period of shelf life, more preferably less than about 85%, more preferably less than about 80%, more preferably less than about 75%, more preferably less than about 70%, more preferably less than about 60%, more preferably less than about 50%, more preferably less than about 40%, more preferably less than about 30%, more preferably less than about 20%, and most preferably less than about 10%.

Preferably, pharmaceutically-acceptable antioxidants comprise one or more of an amino acid sulfite (e.g L-lysine sulfite), ascorbic acid, ascorbyl palmitate, benzotriazol, butylhydroxyanisole (BHA), butylhydroxytoluene (BHT), citric acid, cysteine, cysteine hydrochloride, disodium calcium ethylenediaminetetraacetate, disodium ethylenediaminetetraacetate, dithiothreitol, DL-alpha-tocopherol, erythorbic acid, ethoxyquin, ethylenediaminetetraacetic acid salts, fumaric acid, glutathione, guaiac, homocysteine, isopropyl citrate, N-acetylcysteine, mercaptoethane sulfonic acid, L-ascorbate stearate esters, monothioglycerol, nordihydroguaiaretic acid (NDGA), palmitic acid ascorbic acid, pentaerythrityl-tetrakis[3-(3,5-di-t-butyl-4-hydroxyphenyl)propionate]2-mercaptobenzimidazole, cysteine ethyl ester, dithiothreitol, potassium dichloroisocyanurate, propyl gallate, rongalite (CH2OHSO2Na), sodium ascorbate, sodium bisulfite, sodium edetate, sodium erythorbate, sodium hydrogen sulfite, sodium metabisulfite, sodium pyrosulfite 1,3-butylene glycol, sodium sulfite, methionine, thioglycolic acid, sodium thioglycolate, sodium thiosulfate, soybean lecithin, tert-butyl hydroquinone, thioglycerol, thiourea, TPGS (tocopherol polyethylene glycol succinate), vitamin E and derivatives thereof, α-thioglycerin, and/or salts thereof. Preferably, the antioxidant comprises sodium bisulfite or sodium metabisulfite. In other preferred embodiments, the composition is free of sulfites such as sodium bisulfite or sodium metabisulfite.

According to some preferred embodiments, the antioxidant may comprise a sulfur-containing organic compound. Preferably, the sulfur-containing organic compound is a thiol-containing organic compound. As used herein, the term "organic compound" refers to a compound belonging to the class of compounds characterized by their inclusion of carbon atoms in their molecular backbone. The term "thiol" refers to a carbon-bonded sulfhydryl group. Examples of sulfur-containing organic compounds suitable for use in accordance with the invention include, but are not limited to, cysteine, N-acetylcysteine, glutathione, methionine, monothioglycerol, cysteine ethyl ester, thioglycolic acid, thiolactic acid, dithiothreitol, reduced glutathione, mercaptoethane sulfonic acid, and salts thereof.

According to some aspects, the composition may have an initial active agent overage that is reduced when compared with a composition wherein the antioxidant is not present and/or is different than the antioxidant of the present invention. As used herein, "overage" refers to the amount of a component present in a composition that is more than (or "over") the amount indicated on the label for the composition. For example, traditional epinephrine-containing compositions may have an overage of up to 25% of the amount indicated on the label. Indeed, the USP 39 monograph for epinephrine injections in water requires a formulation to contain no less than 90.0% and no more than 115.0% of the labeled amount of epinephrine. That is, the USP 39 monograph allows for up to a 25% difference between a label claim and the actual amount.

According to some aspects, the present composition may have an initial active agent overage of less than about 20%, preferably less than about 19%, more preferably less than about 18%, more preferably less than about 17%, more preferably less than about 16%, more preferably less than about 15%, more preferably less than about 14%, more preferably less than about 13%, more preferably less than about 12%, more preferably less than about 11%, more preferably less than about 10%, more preferably less than about 9%, more preferably less than about 8%, more preferably less than about 7%, more preferably less than about 6%, more preferably less than about 5%, more preferably less than about 4%, more preferably less than about 3%, more preferably less than about 2%, more preferably less than about 1%, and most preferably about 0%.

The present invention provides a composition that may include one or more transition metal complexing agents.

In some embodiments, the transition metal complexing agent may be a chelating agent. The term "chelating agent" refers to a substance capable of chelation, i.e, the formation or presence of two or more separate coordinate bonds between a polydentate ligand and a single central atom.

In some embodiments, the transition metal complexing agent may reduce the catalytic activity of trace metals present in the composition. In some embodiments, the transition metal complexing agent may chelate trace metals in the composition that may otherwise increase and/or accelerate the degradation of components in the composition. Examples of trace metals include, but are not limited to, iron, magnesium, lithium, zinc, copper, chromium, nickel, cobalt, vanadium, arsenic, molybdenum, manganese, selenium, and calcium.

In some embodiments, the transition metal complexing agent may chelate trace metals in the composition that may otherwise increase and/or accelerate degradant formation in the composition. In some embodiments, the transition metal complexing agent may inhibit the formation of degradants formed from the interaction of epinephrine, bisulfite, and oxygen. In some embodiments, these degradants comprise one or more of Impurity A, Impurity B, and Unknown C.

In some embodiments, the concentration of the transition metal complexing agent present in the composition may be such that the concentration of Impurity A, Impurity B, or Unknown C is about 1% or less of the composition after a certain period of shelf life, preferably about 0.9% or less, more preferably about 0.8% or less, more preferably about 0.7% or less, more preferably about 0.6% or less, more preferably about 0.5% or less, more preferably about 0.4% or less, more preferably about 0.3% or less, more preferably about 0.2% or less, and most preferably about 0.1% or less.

In some embodiments, the transition metal complexing agent may be present at the lowest concentration that reduces and/or inhibits degradation of other components of the composition. In some embodiments, the transition metal complexing agent may be present in the composition at a concentration of about 0.1 and 0.5 mg/mL, preferably in the range of about 0.1 and 0.4 mg/mL, more preferably in the range of about 0.1 and 0.3 mg/mL, and most preferably about 0.2 mg/mL.

Preferably, transition metal complexing agents comprise one or more of TPA (Tris[(2-pyridyl)methyl]amine), phanquinone (4,7-phenanthroline-5,6-dione), clioquinol (PN Gerolymatos SA), chloroquinol, penicillamine, trientine, N,N'-diethyldithiocarbamate (DDC), 2,3,2'-tetraamine (2,3, 2'-tet), neocuproine, N,N,N',N'-tetrakis(2-pyridylmethyl) ethylenediamine (TPEN), 1,10-phenanthroline (PHE), tetraethylenepentamine (TEPA), triethylene tetraamine and tris (2-carboxyethyl)phosphine (TCEP), bathophenanthroline disulfonic acid (BPADA), Disodium Edetate Dihydrate (EDTA), ethylene glycol (bis) aminoethyl ether tetra acetic acid (EGTA), nitrilotriacetic acid, TIRON™, N,N-bis(2-hydroxyethyl)glycine (bicine), O,O'-bis(2-aminophenyl ethylene glycol) ethylenediamine-N,N,N',N'-tetraacetic acid (BAPTA), trans-1,2-diamino cyclohexane-ethylenediamine-N, N, N', N'-tetraacetic acid (CyDTA), 1,3-diamino-2-hydroxy-propane-ethylenediamine-N,N,N', N'-tetraacetic acid (DPTA-OH), ethylene-diamine-N,N'-dipropionic acid dihydrochloride (EDDP), ethylenediamine-N,N'-bis(methylenephosphonic acid) hemihydrate (EDDPO), ethylenediamine-N,N,N',N'-tetrakis(methylenephosphonic acid) (EDTPO), N,N'-bis(2-hydroxybenzyl)ethylene diamine-N,N'-diacetic acid (HBED), 1,6-hexamethylenediamine-N,N,N',N'-tetraacetic acid (HDTA, or HEDTA), N-(2-hydroxyethyl)iminodiacetic acid (HIDA), iminodiacetic acid (IDA), 1,2-diaminopropane-N,N,N',N'-tetraacetic acid (methyl-EDTA), nitriltriacetic acid (NTA), nitrilotripropionic acid (NTP), nitrilotris (methylenephosphonic acid) trisodium salt (NTPO), triethylenetetramine-N,N,N',N''',N'''-hexaacetic acid (TTHA), bathocuproine, bathophenanthroline, TETA, citric acid, salicylic acid, and/or malic acid, including analogues, derivatives, and pharmaceutically acceptable salts thereof. Preferably, the metal complexing agent comprises EDTA.

The present invention provides a composition that may include one or more pH lowering agent. The term "pH lowering agent" refers to a component of a composition selected to lower the composition's pH. In some embodiments, the pH lowering agent may be present in the composition such that the composition's pH is in a pharmaceutically acceptable range (i.e., not toxic or producing unacceptable side effects).

In some embodiments, the pH lowering agent may convert the active agent into a salt that is soluble in the composition. In some embodiments, the pH lowering agent may convert epinephrine into a hydrochloride salt.

In some embodiments, the pH lowering agent may be present at a concentration in the composition such that the composition's pH is within the limit on total acidity imposed by the USP 37-NF 32, S2, monograph. In some embodiments, the pH lowering agent may be present in the composition at a concentration of in the range of about 0.001 to 1 mg/mL, more preferably in the range of about 0.001 to 0.20 mg/mL, more preferably in the range of about 0.001 to 0.10 mg/mL, more preferably in the range of about 0.001 to 0.050 mg/mL and most preferably about 0.025 mg/mL. In some embodiments, the pH lowering agent may be present in the range of about 0.1 to 1 mg/mL, preferably in the range of about 0.1 to 0.5 mg/mL, and most preferably about 0.25 mg/mL.

Preferably, the pH lowering agent comprises one or more of acetic acid, adipic acid, ascorbic acid, citric acid, hydrochloric acid, lactic acid, malic acid, monopotassium phosphate, monosodium phosphate, phosphoric acid, pyrophosphoric acid, succinic acid, sulfuric acid, and or tartaric acid. Preferably, the pH lowering agent comprises hydrochloric acid. In certain embodiments, the pH lowering agent may be a portion of the buffer system in conjugation with a pH raising agent.

The present invention provides for a composition that may comprise at least one tonicity regulating agent. The term "tonicity" refers to the effective osmotic pressure equivalent of a solution or composition. In some embodiments, the tonicity regulating agent may be present in the composition to maintain the tonicity of the composition in a physiological acceptable range. In some embodiments, the tonicity regulating agent may be an osmotic pressure regulating agent.

Preferably, the tonicity regulating agent comprises one or more of glucose, glycerin, hydroxypropyl methyl cellulose, mannitol, polysorbate, propylene glycol, sodium bromide, sodium chloride, sodium iodide, sorbitol, urea, xylitol, and/or combinations thereof. Preferably, the tonicity regulating agent comprises sodium chloride.

In some embodiments, the tonicity regulating agent may be present in the composition at a concentration of in the range of about 4 and 9 mg/mL, preferably in the range of about 5 and 8 mg/mL, and most preferably in the range of about 6 and 7.5 mg/mL. In some embodiments, the tonicity regulating agent may be present at a concentration of about 7.3 mg/mL. In some embodiments, the tonicity regulating agent may be present at a concentration of about 6.15 mg/mL.

The present invention provides for a composition that may optionally comprise one or more preservatives. The term "preservative" refers to a substance present in a composition which can, at least in part, prevent and/or reduce decomposition of the composition. In some embodiments, the preservative may prevent and/or reduce decomposition of the composition by microbial growth in the composition. Preferably, the preservative is pharmaceutically acceptable. In some embodiments, the composition is free of preservatives.

In some embodiments, the preservative may be present in the composition at a concentration that allows for a multi-dose formulation of the composition. In some embodiments, the preservative may be present in the composition at a concentration that prevents and/or reduces decomposition of unused portions of the composition in a multi-dose formulation. In some embodiments, the preservative may allow for up to about 14 days of use, preferably up to about 30 days of use, more preferably up to about 60 days of use, and most preferably up to about 90 days of use of a multi-dose formulation of the composition.

In some embodiments, the preservative may be present in the composition at a concentration of in the range of about 1 to 10 mg/mL, preferably in the range of about 3 and 7 mg/mL, more preferably in the range of about 4 and 6 mg/mL, more preferably in the range of about 4.5 and 5.5 mg/mL, and most preferably at about 5 mg/mL.

Preferably, preservatives comprise one or more of benzalkonium chloride, benzethonium chloride, benzoic acid, benzyl alcohol, benzyl paraben, bronopol, butyl paraben, cetrimide, cetylpyridinium chloride, chlorbutanol, chlorhexidine, chlorocresol, chloroxylenol, cresol, ethyl alcohol, ethyl paraben, ethylparaben, glycerin, hexetidine, imidurea, isobutyl paraben, meta-cresol, methyl paraben, methylparaben, phenol, phenoxyethanol, phenylethyl alcohol, phenylmercuric nitrate, p-hydroxybenzoic acid esters, polyhexamethylene biguanide ("PHMB"), potassium sorbate, propyl paraben, propylene glycol, sodium benzoate, sodium perborate, sodium propionate, sorbic acid, stabilized thimerosal, and/or thimerosal. Preferably, the preservative comprises chlorobutanol.

The present invention provides for a composition that can optionally comprise one or more solvents. In some embodiments, the solvent may be acceptable for pharmaceutical administration. Examples of methods of pharmaceutical administration include, but are not limited to, subcutaneous, intracameral, intravenous, and intramuscular injection, infusion, intra-arterial administration, intracardiac injection, endotracheal administration, intraosseous administration, oral inhalation, topical administration, and as ophthalmic irrigation.

Preferably, the solvent comprises one or more of acetic acid, acetone, acetonitrile, animal oil, aqueous buffer, benzene, bisabolol, butanol, carbon tetrachloride, chlorobenzene, chloroform, dimethylformamide, dioxane, essential oil, ethanol, ethyl acetate, ethyl oleate, ethylene chloride, fatty acid esters, glycerin, glycofurol, hexane, hydrogenated vegetable oil, isopropanol, isopropyl alcohol, isopropyl myristate, isopropyl palmitate, methanol, methylene chloride, mineral oil, polyethylene glycol, polyol, propylene glycol, silicone fluid glyceride, squalane, terpene, tetrahydrofuran, toluene, triacetin, tributyl citrate, triethyl citrate, vegetable oil, and/or water. Preferably the solvent comprises water.

In some embodiments, the solvent may be present in an amount that brings the composition to a final volume which is suitable for administration. In some embodiments, the final volume may be 1 mL. In some embodiments, the final volume may be 30 mL.

The present invention provides for a composition that may have a low level of impurities. The term "impurity" refers to an undesired substance in a composition. In some embodiments, an amount of impurities may be present in an initial composition and/or may be formed after a certain period of shelf life of a composition. In some embodiments, impurities may be formed via degradation of one or more components of the composition. Sources of degradation include, but are not limited to, oxidation, racemization, sulfite addition, visible light, ultraviolet light, moisture, heat, changes in pH, and composition component interactions. Unless indicated otherwise, the percentages of impurities expressed herein are expressed as % w/w of the active agent.

In some embodiments, the composition may have no more than about 20% of total impurities after a certain period of shelf life, more preferably no more than about 19.5%, more preferably no more than about 19%, more preferably no more than about 18.5%, preferably no more than about 18%, more preferably no more than about 17.5%, more preferably no more than about 17%, more preferably no more than about 16.5%, more preferably no more than about 16%, more preferably no more than about 15.5%, more preferably no more than about 15%, more preferably no more than about 14.5%, more preferably no more than about 14%, more preferably no more than about 13.5%, more preferably no more than about 13%, more preferably no more than about 12.5%, more preferably no more than about 12%, more preferably no more than about 11.5%, more preferably no more than about 11%, more preferably no more than about 10.5%, more preferably no more than about 10%, more preferably no more than about 9.5%, more preferably no more than about 9%, more preferably no more than about 8.5%, more preferably no more than about 8%, more preferably no more than about 7.5%, more preferably no more than about 7%, more preferably no more than about 6.5%, more preferably no more than about 6%, more preferably no more than about 5.5%, and most preferably no more than about 5%.

In some embodiments, the composition may have no more than about 20% of total impurities after a certain period of shelf life, preferably no more than about 19.9%, more preferably no more than about 19.8%, more preferably no more than about 19.7%, more preferably no more than about 19.6%, more preferably no more than about 19.5%, more preferably no more than about 19.4%, more preferably no more than about 19.3%, more preferably no more than about 19.2%, more preferably no more than about 19.1%, more preferably no more than about 19%, more preferably no more than about 18.9%, more preferably no more than about 18.8%, more preferably no more than about 18.7%, more preferably no more than about 18.6%, more preferably no more than about 18.5%, more preferably no more than about 18.4%, more preferably no more than about 18.3%, more preferably no more than about 18.2%, more preferably no more than about 18.1%, more preferably no more than about 18%, more preferably no more than about 17.9%, more preferably no more than about 17.8%, more preferably no more than about 17.7%, more preferably no more than about 17.6%, more preferably no more than about 17.5%, more preferably no more than about 17.4%, more preferably no more than about 17.3%, more preferably no more than about 17.2%, more preferably no more than about 17.1%, more preferably no more than about 17%, more preferably no more than about 16.9%, more preferably no more than about 16.8%, more preferably no more than about 16.7%, more preferably no more than about 16.6%, more preferably no more than about 16.5%, more preferably no more than about 16.4%, more preferably no more than about 16.3%, more preferably no more than about 16.2%, more preferably no more than about 16.1%, more preferably no more than about 16%, more preferably no more than about 15.9%, more preferably no more than about 15.8%, more preferably no more than about 15.7%, more preferably no more than about 15.6%, more preferably no more than about 15.5%, more preferably no more than about 15.4%, more preferably no more than about 15.3%, more preferably no more than about 15.2%, more preferably no more than about 15.1%, more preferably no more than about 15%, more preferably no more than about 14.9%, more preferably no more than about 14.8%, more preferably no more than about 14.7%, more preferably no more than about 14.6%, more preferably no more than about 14.5%, more preferably no more than about 14.4%, more preferably no more than about 14.3%, more preferably no more than about 14.2%, more preferably no more than about 14.1%, more preferably no more than about 14%, more preferably no more than about 13.9%, more preferably no more than about 13.8%, more preferably no more than about 13.7%, more preferably no more than about 13.6%, more preferably no more than about 13.5%, more preferably no more than about 13.4%, more preferably no more than about 13.3%, more preferably no more than about 13.2%, more preferably no more than about 13.1%, more preferably no more than about 13%, more preferably no more than about 12.9%, more preferably no more than about 12.8%, more preferably no more than about 12.7%, more preferably no more than about 12.6%, more preferably no more than about 12.5%, more preferably no more than about 12.4%, more preferably no more than about 12.3%, more preferably no more than about 12.2%, more preferably no more than about 12.1%, more preferably no more than about 12%, more preferably no more than about 11.9%, more preferably no more than about 11.8%, more preferably no more than about 11.7%, more preferably no more than about 11.6%, more preferably no more than about 11.5%, more preferably no more than about 11.4%, more preferably no more than about 11.3%, more preferably no more than about 11.2%, more preferably no more than about 11.1%, more preferably no more than about 11%, more preferably no more than about 10.9%, more preferably no more than about 10.8%, more preferably no more than about 10.7%, more preferably no more than about 10.6%, more preferably no more than about 10.5%, more preferably no more than about 10.4%, more preferably no more than about 10.3%, more preferably no more than about 10.2%, more preferably no more than about 10.1%, more preferably no more than about 10%, more preferably no more than about 9.9%, more preferably no more than about 9.8%, more preferably no more than about 9.7%, more preferably no more than about 9.6%, more preferably no more than about 9.5%, more preferably no more than about 9.4%, more preferably no more than about 9.3%, more preferably no more than about 9.2%, more preferably no more than about 9.1%, more preferably no more than about 9%, more preferably no more than about 8.9%, more preferably no more than about 8.8%, more preferably no more than about 8.7%, more preferably no more than about 8.6%, more preferably no more than about 8.5%, more preferably no more than about 8.4%, more preferably no more than about 8.3%, more preferably no more than about 8.2%, more preferably no more than about 8.1%, more preferably no more than about 8%, more preferably no more than about 7.9%, more preferably no more than about 7.8%, more preferably no more than about 7.7%, more preferably no more than about 7.6%, more preferably no more than about 7.5%, more preferably no more than about 7.4%, more preferably no more than about 7.3%, more preferably no more than about 7.2%, more preferably no more than about 7.1%, more preferably no more than about 7%, more preferably no more than about 6.9%, more preferably no more than about 6.8%, more preferably no more than about 6.7%, more preferably no more than about 6.6%, more preferably no more than about 6.5%, more preferably no more than about 6.4%, more preferably no more than about 6.3%, more preferably no more than about 6.2%, more preferably no more than about 6.1%, more preferably no more than about 6%, more preferably no more than about 5.9%, more preferably no more than about 5.8%, more preferably no more than about 5.7%, more preferably no more than about 5.6%, more preferably no more than about 5.5%, more preferably no more than about 5.4%, more preferably no more than about 5.3%, more preferably no more than about 5.2%, more preferably no more than about 5.1%, more preferably no more than about 5%, more preferably no more than about 4.9%, more preferably no more than about 4.8%, more preferably no more than about 4.7%, more preferably no more than about 4.6%, more preferably no more than about 4.5%, more preferably no more than about 4.4%, more preferably no more than about 4.3%, more preferably no more than about 4.2%, more preferably no more than about 4.1%, more preferably no more than about 4%, more preferably no more than about 3.9%, more preferably no more than about 3.8%, more preferably no more than about 3.7%, more preferably no more than about 3.6%, more preferably no more than about 3.5%, more preferably no more than about 3.4%, more preferably no more than about 3.3%, more preferably no more than about 3.2%, more preferably no more than about 3.1%, more preferably no more than about 3%, more preferably no more than about 2.9%, more preferably no more than about 2.8%, more preferably no more than about 2.7%, more preferably no more than about 2.6%, more preferably no more than about 2.5%, more preferably no more than about 2.4%, more preferably no more than about 2.3%, more preferably no more than about 2.2%, more preferably no more than about 2.1%, more preferably no more than about 2%, more preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, and most preferably about 0%.

In some embodiments, the concentration of impurities present in the composition after a certain period of shelf life may be attributed at least partially to degradation of components of the composition. In some embodiments, the concentration of impurities present in the composition at the end of shelf life may be attributed at least partially to epinephrine degradation. In some embodiments, epinephrine degradation may be a result of physical or chemical stress. Examples of stresses include, but are not limited to, oxygen, pH, bisulfite, light, process surface compatibility, and soluble trace metals.

In some embodiments, components of the composition may be present at a concentration that lowers the amount of impurities after a certain period of shelf life that would otherwise be present in the absence of the components. In some embodiments, components of the composition may be present at a concentration that at least partially inhibits formation of impurities in the composition.

The present invention provides for a composition that may have a low level of D-epinephrine.

In some embodiments, the concentration of D-epinephrine in the composition after a certain period of shelf life may be no more than about 9.5%, preferably no more than about 9%, more preferably no more than about 8.5%, more preferably no more than about 8%, more preferably no more than about 7.5%, more preferably no more than about 7%, more preferably no more than about 6.5%, more preferably no more than about 6%, more preferably no more than about 5.5%, more preferably no more than about 5%, more preferably no more than about 4.5%, more preferably no more than about 4%, more preferably no more than about 3.5%, more preferably no more than than about 3%, more preferably no more than about 2.5%, more preferably no more than about 2%, more preferably no more than about 1.5%, more preferably no more than about 1%, and most preferably no more than about 0.5%.

In some embodiments, the concentration of D-epinephrine in the composition after a period of shelf life may be no more than about 9.5%, preferably no more than about 9.4%, more preferably no more than about 9.3%, more preferably no more than about 9.2%, more preferably no more than about 9.1%, more preferably no more than about 9%, more preferably no more than about 8.9%, more preferably no more than about 8.8%, more preferably no more than about 8.7%, more preferably no more than about 8.6%, more preferably no more than about 8.5%, more preferably no more than about 8.4%, more preferably no more than about 8.3%, more preferably no more than about 8.2%, more preferably no more than about 8.1%, more preferably no more than about 8%, more preferably no more than about 7.9%, more preferably no more than about 7.8%, more preferably no more than about 7.7%, more preferably no more than about 7.6%, more preferably no more than about 7.5%, more preferably no more than about 7.4%, more preferably no more than about 7.3%, more preferably no more than about 7.2%, more preferably no more than about 7.1%, more preferably no more than about 7%, more preferably no more than about 6.9%, more preferably no more than about 6.8%, more preferably no more than about 6.7%, more preferably no more than about 6.6%, more preferably no more than about 6.5%, more preferably no more than about 6.4%, more preferably no more than about 6.3%, more preferably no more than about 6.2%, more preferably no more than about 6.1%, more preferably no more than about 6%, more preferably no more than about 5.9%, more preferably no more than about 5.8%, more preferably no more than about 5.7%, more preferably no more than about 5.6%, more preferably no more than about 5.5%, more preferably no more than about 5.4%, more preferably no more than about 5.3%, more preferably no more than about 5.2%, more preferably no more than about 5.1%, more preferably no more than about 5%, more preferably no more than about 4.9%, more preferably no more than about 4.8%, more preferably no more than about 4.7%, more preferably no more than about 4.6%, more preferably no more than about 4.5%, more preferably no more than about 4.4%, more preferably no more than about 4.3%, more preferably no more than about 4.2%, more preferably no more than about 4.1%, more preferably no more than about 4%, more preferably no more than about 3.9%, more preferably no more than about 3.8%, more preferably no more than about 3.7%, more preferably no more than about 3.6%, more preferably no more than about 3.5%, more preferably no more than about 3.4%, more preferably no more than about 3.3%, more preferably no more than about 3.2%, more preferably no more than about 3.1%, more preferably no more than about 3%, more preferably no more than about 2.9%, more preferably no more than about 2.8%, more preferably no more than about 2.7%, more preferably no more than about 2.6%, more preferably no more than about 2.5%, more preferably no more than about 2.4%, more preferably no more than about 2.3%, more preferably no more than about 2.2%, more preferably no more than about 2.1%, more preferably no more than about 2%, more preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, more preferably no more than about 0.09%, more preferably no more than about 0.08%, more preferably no more than about 0.07%, more preferably no more than about 0.06%, more preferably no more than about 0.05%, more preferably no more than about 0.04%, more preferably no more than about 0.03%, more preferably no more than about 0.02%, and most preferably no more than about 0.01%.

In some embodiments, the initial concentration of D-epinephrine in the composition may be no more than about 2.5%, preferably no more than about 2%, more preferably no more than about 1.5%, more preferably no more than about 1%, and most preferably no more than about 0.5%.

In some embodiments, components of the composition may be present at concentrations that reduce the formation of D-epinephrine that would otherwise occur in the absence of the components. In some embodiments, components of the composition may be present at concentrations that reduce D-epinephrine formation by at least about 15%, more preferably at least about 33%, and most preferably at least about 50%.

In some embodiments, components of the composition may be present at a concentration that reduces the rate and/or extent of D-epinephrine formation after a certain period of shelf life. In some embodiments, components of the composition may reduce D-epinephrine formation by raising the initial pH of the composition and/or by increasing the pH range of the composition over shelf life. In some embodiments, the pH of the composition may be raised at least partially by the pH raising agent. Preferably, the raised pH of the composition does not result in large increases of other degradants of epinephrine.

The present invention provides for a composition that may have a low level of epinephrine sulfonic acid (ESA). In some embodiments, the concentration of ESA in the composition after a certain period of shelf life may be no more than about 14.5%, preferably no more than about 14%, more preferably no more than about 13.5%, more preferably no more than about 13%, more preferably no more than about 12.5%, more preferably no more than about 12%, more preferably no more than about 11.5%, more preferably no more than about 11%, more preferably no more than about 10.5%, more preferably no more than about 10%, more preferably no more than about 9.5%, more preferably no more than about 9%, more preferably no more than about 8.5%, more preferably no more than about 8%, more preferably no more than about 7.5%, more preferably no more than about 7%, more preferably no more than about 6.5%, more preferably no more than about 6%, and most preferably no more than about 5.5%.

In some embodiments, the concentration of ESA in the composition after a certain period of shelf life may be no more than about 14.5%, preferably no more than about 14.4%, more preferably no more than about 14.3%, more preferably no more than about 14.2%, more preferably no more than about 14.1%, more preferably no more than about 14%, more preferably no more than about 13.9%, more preferably no more than about 13.8%, more preferably no more than about 13.7%, more preferably no more than about 13.6%, more preferably no more than about 13.5%, more preferably no more than about 13.4%, more preferably no more than about 13.3%, more preferably no more than about 13.2%, more preferably no more than about 13.1%, more preferably no more than about 13%, more preferably no more than about 12.9%, more preferably no more than about 12.8%, more preferably no more than about 12.7%, more preferably no more than about 12.6%, more preferably no more than about 12.5%, more preferably no more than about 12.4%, more preferably no more than about 12.3%, more preferably no more than about 12.2%, more preferably no more than about 12.1%, more preferably no more than about 12%, more preferably no more than about 11.9%, more preferably no more than about 11.8%, more preferably no more than about 11.7%, more preferably no more than about 11.6%, more preferably no more than about 11.5%, more preferably no more than about 11.4%, more preferably no more than about 11.3%, more preferably no more than about 11.2%, more preferably no more than about 11.1%, more preferably no more than about 11%, more preferably no more than about 10.9%, more preferably no more than about 10.8%, more preferably no more than about 10.7%, more preferably no more than about 10.6%, more preferably no more than about 10.5%, more preferably no more than about 10.4%, more preferably no more than about 10.3%, more preferably no more than about 10.2%, more preferably no more than about 10.1%, more preferably no more than about 10%, more preferably no more than about 9.9%, more preferably no more than about 9.8%, more preferably no more than about 9.7%, more preferably no more than about 9.6%, more preferably no more than about 9.5%, more preferably no more than about 9.4%, more preferably no more than about 9.3%, more preferably no more than about 9.2%, more preferably no more than about 9.1%, more preferably no more than about 9%, more preferably no more than about 8.9%, more preferably no more than about 8.8%, more preferably no more than about 8.7%, more preferably no more than about 8.6%, more preferably no more than about 8.5%, more preferably no more than about 8.4%, more preferably no more than about 8.3%, more preferably no more than about 8.2%, more preferably no more than about 8.1%, more preferably no more than about 8%, more preferably no more than about 7.9%, more preferably no more than about 7.8%, more preferably no more than about 7.7%, more preferably no more than about 7.6%, more preferably no more than about 7.5%, more preferably no more than about 7.4%, more preferably no more than about 7.3%, more preferably no more than about 7.2%, more preferably no more than about 7.1%, more preferably no more than about 7%, more preferably no more than about 6.9%, more preferably no more than about 6.8%, more preferably no more than about 6.7%, more preferably no more than about 6.6%, more preferably no more than about 6.5%, more preferably no more than about 6.4%, more preferably no more than about 6.3%, more preferably no more than about 6.2%, more preferably no more than about 6.1%, more preferably no more than about 6%, more preferably no more than about 5.9%, more preferably no more than about 5.8%, more preferably no more than about 5.7%, more preferably no more than about 5.6%, more preferably no more than about 5.5%, more preferably no more than about 5.4%, more preferably no more than about 5.3%, more preferably no more than about 5.2%, more preferably no more than about 5.1%, more preferably no more than about 5.0%, more preferably no more than about 4.9%, more preferably no more than about 4.8%, more preferably no more than about 4.7%, more preferably no more than about 4.6%, more preferably no more than about 4.5%, more preferably no more than about 4.4%, more preferably no more than about 4.3%, more preferably no more than about 4.2%, more preferably no more than about 4.1%, more preferably no more than about 4.0%, more preferably no more than about 3.9%, more preferably no more than about 3.8%, more preferably no more than about 3.7%, more preferably no more than about 3.6%, more preferably no more than about 3.5%, more preferably no more than about 3.4%, more preferably no more than about 3.3%, more preferably no more than about 3.2%, more preferably no more than about 3.1%, more preferably no more than about 3.0%, more preferably no more than about 2.9%, more preferably no more than about 2.8%, more preferably no more than about 2.7%, more preferably no more than about 2.6%, more preferably no more than about 2.5%, more preferably no more than about 2.4%, more preferably no more than about 2.3%, more preferably no more than about 2.2%, more preferably no more than about 2.1%, more preferably no more than about 2.0%, more preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1.0%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, and most preferably about 0%.

In some embodiments, the initial concentration of ESA in the composition may be no more than about 0.5%, preferably no more than about 0.2%, more preferably no more than about 0.1%, more preferably no more than about 0.05%, and most preferably no more than about 0.025%.

In some embodiments, ESA formation may be influenced by an oxygen-dependent mechanism such that reducing oxygen accessible to the composition may reduce the rate of ESA formation. In some embodiments, oxygen present in the headspace of a vial containing the composition may be reduced by replacing some or all of the oxygen with a gas other than oxygen, preferably an inert gas, thereby at least partially reducing the rate of ESA production. In some embodiments, some or all of the oxygen present in the headspace of a vial containing the composition may be replaced with nitrogen and/or argon.

In some embodiments, the headspace gas of the composition is manipulated such that degradation of components in the composition is minimized. The term "headspace" refers to the gas space above the product in a container. The headspace gas may be manipulated in order to reduce the amount of oxygen present therein. In some embodiments, the amount of oxygen in the headspace gas is no more than about 15% v/v of the total gas, preferably no more than about 13%, more preferably no more than about 10%, more preferably no more than about 5%, more preferably no more than about 2.5%, more preferably no more than about 1%, and most preferably about 0%.

In some embodiments of the present invention, the concentrations of certain components of the composition may be reduced such that the concentration of ESA in the composition after a period of shelf life is reduced. In some embodiments, the concentration of ESA present in the composition after a period of shelf life is reduced at least partially by reducing the initial concentration of antioxidant in the composition. In some embodiments, the concentrations of certain components of the composition, such as initial concentration of antioxidant, are reduced such that the rate of ESA production is reduced by at least about 25%, more preferably at least about 50%, and most preferably at least about 75% after a certain period of shelf life, as compared to a composition in which the certain components are not present.

The present invention provides for a composition that may have a low level of oxidative degradants. The term "oxidative degradant" refers to any impurity that may be at least partially attributed to an oxidation reaction involving one or more components of the composition. In some embodiments, the oxidative degradants may be formed via oxidation of epinephrine. Examples of oxidative degradants include, but are not limited to, adrenalone, adrenochrome sulfonate, adrenochrome, adrenolutin, melanins, and analogs thereof.

In some embodiments, the concentration of one of the oxidative degradants in the composition after a certain period of shelf life may be no more than about 1%, preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, more preferably no more than about 0.05%, more preferably no more than about 0.04%, more preferably no more than about 0.03%, more preferably no more than about 0.02%, and most preferably no more than about 0.01%, after a certain period of shelf life.

In some embodiments, the concentration of more than one or all of the oxidative degradants in the composition after a certain period of shelf life may be no more than about 1%, preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, more preferably no more than about 0.1%, more preferably no more than about 0.05%, more preferably no more than about 0.04%, more preferably no more than about 0.03%, more preferably no more than about 0.02%, and most preferably no more than about 0.01%, after a certain period of shelf life.

In some embodiments, the concentration of oxidative degradants present in the composition after a certain period of shelf life may be such that the composition does not undergo a physical change. Examples of physical change include, but are not limited to, color change and insoluble particle formation.

In some embodiments, the rate of formation and/or the concentration of oxidative degradants in the composition may be reduced after a certain period of shelf life by other components of the composition. In some embodiments, the rate of formation and/or the concentration of oxidative degradants in the composition may be reduced by the antioxidant. In some embodiments, the rate of formation and/or the concentration of oxidative degradants in the composition may be reduced by reducing the amount of oxygen accessible to the composition. In some embodiments, the rate of formation and/or the concentration of oxidative degradants in the composition may be reduced by replacing some or all of the oxygen in the headspace of a vial containing the composition with non-oxygen gas, preferably an inert gas such as nitrogen and/or argon.

In some embodiments, the present invention may have low levels of degradants Impurity A, Impurity B, and/or Unknown C.

In some embodiments, Impurity A may be a compound with the following structure:

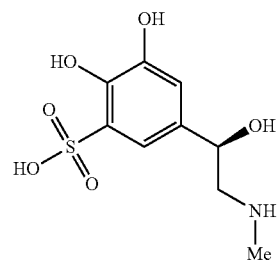 [SMILES: CNC[C@H](O)c1cc(O)c(O)c(S(=O)(=O)O)c1]

In some embodiments, Impurity B may be a compound with the following structure:

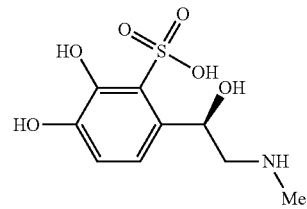 [SMILES: CNC[C@H](O)c1ccc(O)c(O)c1S(=O)(=O)O]

In some embodiments, Unknown C may be characterized by a $\lambda_{max}$ of about 380 nm.

In some embodiments, Unknown C may be characterized by its elution peak using HILIC (Hydrophilic Interaction Liquid Chromatography), which differs from one substance to another.

In some embodiments, Unknown C may be characterized using an isocratic HILIC separation of mixtures according to the conditions described in Tables 1-3.

Table 1 lists the compositions of the mobile phases that may be used for isocratic HILIC separations.

TABLE 1

| Composition of Isocratic Mobile Phases | |
| --- | --- |
| Mobile Phase A | 100 mL Ammonium Formate Buffer 900 mL Acetonitrile |
| Mobile Phase B | 100 mL Ammonium Formate Buffer 400 mL Water 500 mL Acetonitrile |

The Ammonium Formate Buffer of Table 1 may be prepared as follows: 1.5 g of Sodium Chloride, 5.0 mL of Formic Acid, and 3.0 mL of 6N Ammonium Hydroxide is added to 1.0 L of water. The solution may be vacuum filtered through a 0.45 μm nylon membrane. The preparation may be scaled up where necessary.

Table 2 lists different conditions that may be used for isocratic HILIC separations.

TABLE 2

| Isocratic Mobile Phases for HILIC Separation | | |
| --- | --- | --- |
| Isocratic Water % | Mobile Phase A % | Mobile Phase B % |
| 15 | 87.5 | 12.5 |
| 18 | 80 | 20 |
| 22 | 70 | 30 |

An Epinephrine HILIC Impurities Marker Solution (Epi-HILIC IMS) may be prepared by first preparing an Epinephrine/Degradant Bulk Solution as follows: In a clean, clear, 2 L glass bottle, dissolving sodium chloride (6.147 g) and tartaric acid (2.251 g) in about 800 mL of water, adding sodium hydroxide 5.0 N (6.25 mL) to the solution and mixing, adding sodium metabisulfite (1.425 g) to the solution and mixing to dissolve, adding epinephrine (1.1334 g) as a solution in HCl 1.0 N (6.6 mL) to the solution, and then adding water to a final solution weight of 1005.9, and mixing thoroughly. The Epinephrine/Degradant Bulk Solution may then be allowed to sit in a capped bottle in the hood, under fluorescent light with a light exposure at about 1000 lux, for 12 days with lights continuously on.

The Epinephrine HILIC Impurities Marker Solution (Epi-HILIC IMS) may then be prepared in a 500 mL clear glass bottle as follows: adding Epinephrine/Degradant Bulk Solution (500 mL), adding HCl 1.0 N (6.0 mL) and then mixing (with a final pH at 3.2), adding ESA (9.5 mg) and mixing to dissolve, adding adrenochrome (5.6 mg) and mixing to dissolve, preparing adrenalone stock mixture by withdrawing 10 mL of the solution then adding and dissolving adrenalone HCl (4.7 mg), adding adrenalone stock mixture (0.8 mL) back into the bulk mixture, and mixing thoroughly.

An Epinephrine HILIC Impurities Marker Solution (Epi-HILIC IMS) which comprises Unknown C may be analyzed using the conditions listed in Table 3.

TABLE 3

Chromatographic Conditions for Isocratic HILIC Separation

| | |
|---|---|
| Column | SeQuant ZIC HILIC PEEK, 150 × 4.6 mm, 3.5 μm particle size, 100 Å pore size |
| Flow Rate | 1 mL/min |
| Injection Volume | 25 μL |
| Column Temperature | 35° C. |
| Sample preparation | Dilute exactly 1 volume of sample (nominal strength of 1 mg/mL epinephrine) with exactly 3 volumes of acetonitrile. |
| Detector | Signal-280 nm, Bandwidth-10 nm; Reference-Off |
| | Signal-346 nm, Bandwidth-10 nm; Reference-Off |
| | Signal-380 nm, Bandwidth-10 nm; Reference-Off |
| | Signal-292 nm, Bandwidth-10 nm; Reference-Off |
| Run Time | 35 minutes |
| Data Acquisition | Integrate impurities between 0 and 30 minutes |

Tables 4 lists the relevant characteristic peaks of isocratic HILIC separation according to the above specifications at a detection wavelength of 346 nm using the 15% isocratic water preparation according to Table 2.

TABLE 4

Chromatography of the Impurities Marker Solution using isocratic HILIC with 15% water and 346 nM Detection

| | Time (Minutes) | Absorbance (AU) |
|---|---|---|
| Unknown C | approx. 21 | approx. 0.001 |

Tables 5 lists the relevant characteristic peaks of isocratic HILIC separation according to the above specifications at a detection wavelength of 346 nm using the 18% isocratic water preparation according to Table 2.

TABLE 5

Chromatography of the Impurities Marker Solution using isocratic HILIC with 18% water and 346 nM Detection

| | Time (Minutes) | Absorbance (AU) |
|---|---|---|
| Unknown C | approx. 14 | approx. 0.002 |

Table 6 lists the relevant characteristic peaks of isocratic HILIC separation according to the above specifications at a detection wavelength of 346 nm using the 22% isocratic water preparation according to Table 2.

TABLE 6

Chromatography of the Impurities Marker Solution using isocratic HILIC with 22% water and 346 nM Detection

| | Time (Minutes) | Absorbance (AU) |
|---|---|---|
| Unknown C | approx. 8.5 | approx. 0.002 |

Figure 2:
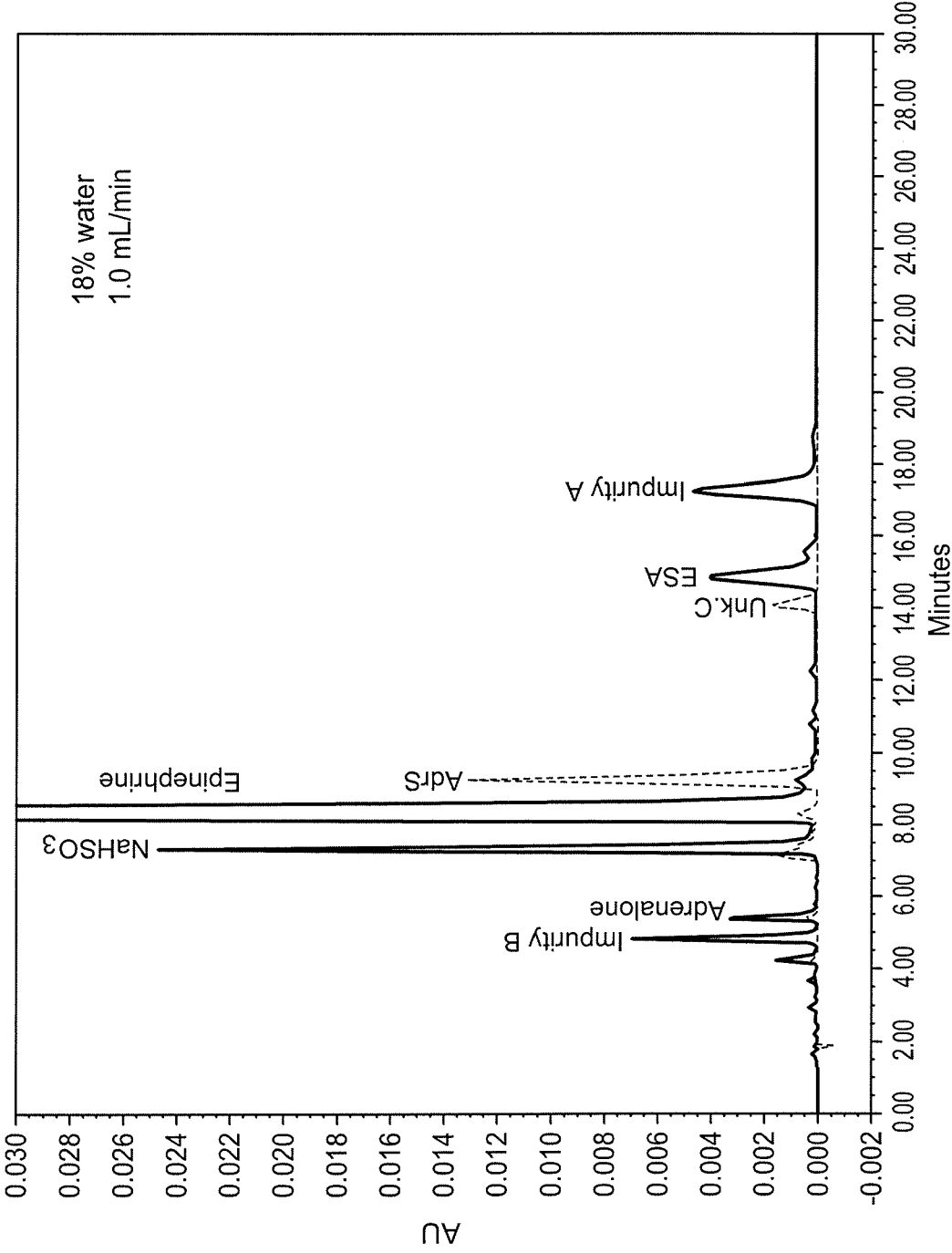
FIG. 2 is a chromatogram of the Impurities Marker Solution using isocratic HILIC with 18% water.
Figure 3:
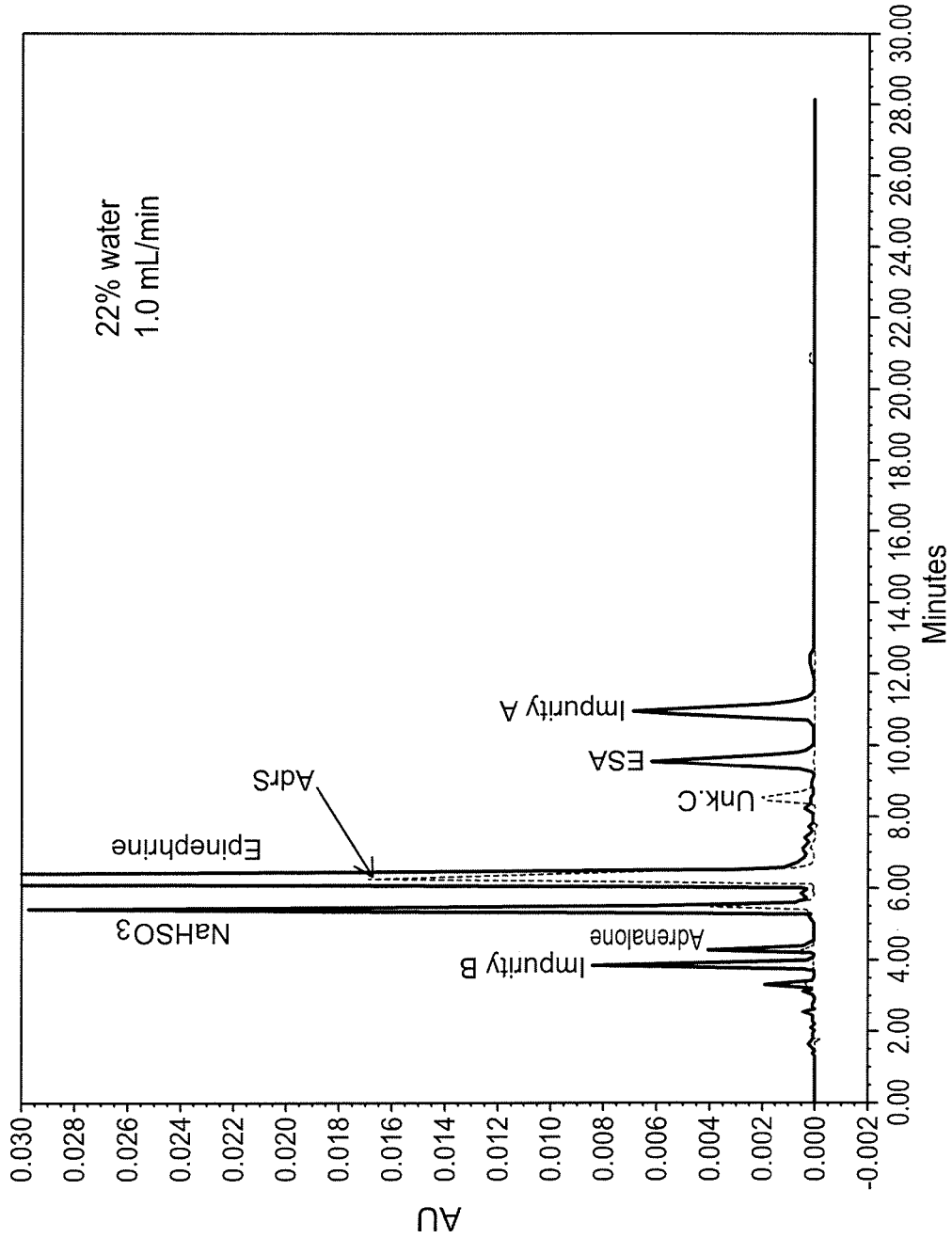
FIG. 3 is a chromatogram of the Impurities Marker Solution using isocratic HILIC with 22% water.

The chromatography outputs of the Impurities Marker Solution using isocratic HILIC as described is also shown in FIG. 1 (15% water), FIG. 2 (18% water), and FIG. 3 (22% water).

In some embodiments, Unknown C may be characterized using a gradient HILIC method. An Epinephrine HILIC Impurities Marker Solution (EpiHILIC IMS) which comprises Unknown C may be analyzed using the conditions listed in Table 7 and 8.

Table 7 lists the compositions of the mobile phases that may be used for gradient HILIC separations.

TABLE 7

Composition of Gradient Mobile Phases

| | |
|---|---|
| Mobile Phase A | 100 mL Ammonium Formate Buffer 900 mL Acetonitrile |
| Mobile Phase A | 100 mL Ammonium Formate Buffer 400 mL Water 500 mL Acetonitrile |

Table 8 lists the solvent program for the gradient HILIC method.

TABLE 8

Solvent program for the gradient HILICmethod.

| | | Mobile Phase Composition | | |
|---|---|---|---|---|
| Time (min) | Flow (mL/min) | Water % | A % | B % |
| Initial | 1.0 | 15.2 | 87 | 13 |
| 12 | 1.0 | 15.2 | 87 | 13 |
| 22 | 1.0 | 22 | 70 | 30 |
| 25 | 1.0 | 22 | 70 | 30 |
| 28 | 1.0 | 15.2 | 87 | 13 |
| 35 | 1.0 | 15.2 | 87 | 13 |

The chromatographic conditions for the gradient HILIC are the same as those listed in Table 3.

Figure 4:
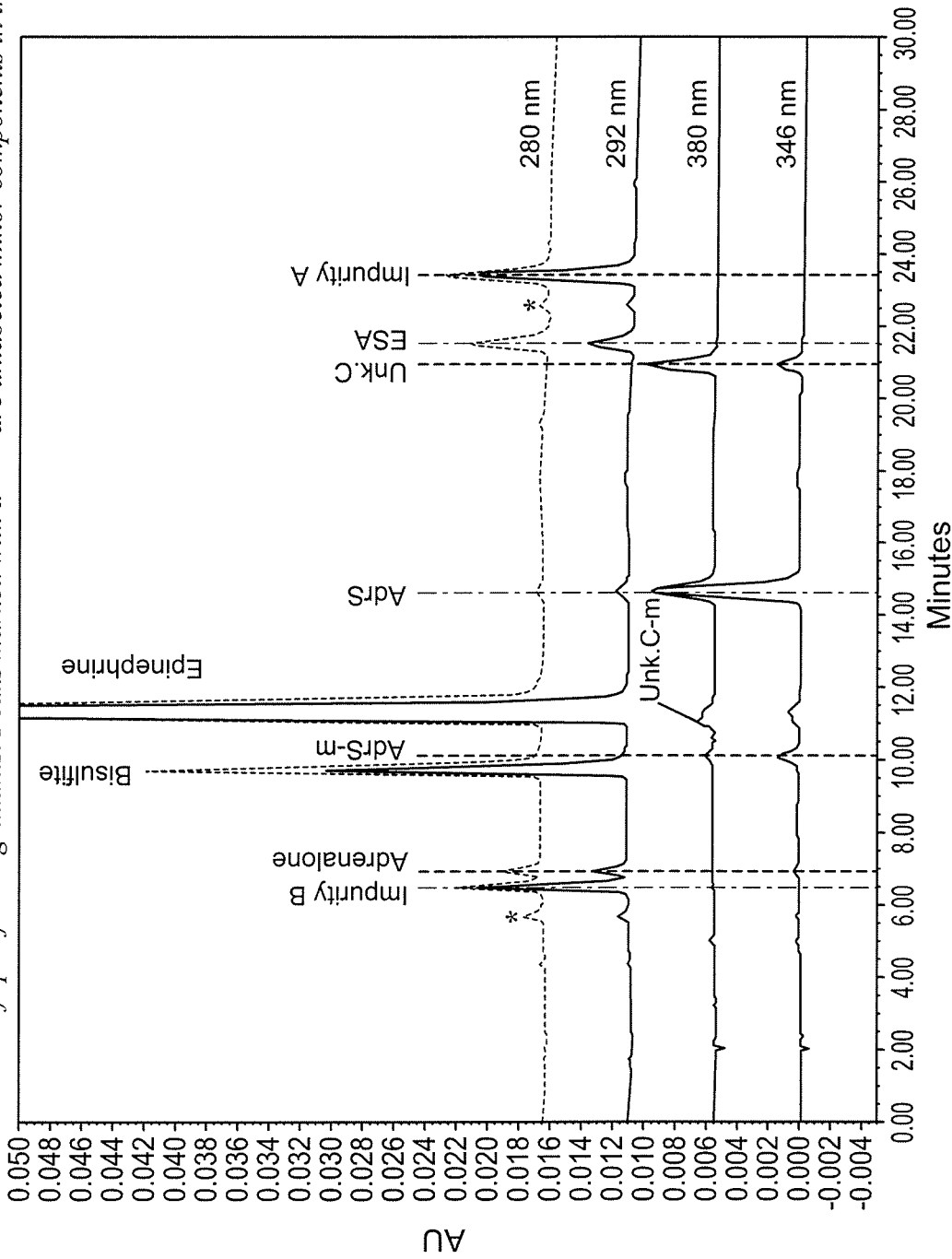
FIG. 4 is a chromatogram of the Impurities Marker Solution using gradient HILIC separation.

The chromatography outputs of the Impurities Marker Solution using gradient HILIC according to the above specifications at detection wavelengths of 280 nm, 292 nm, 346 nm, and 380 nm are shown in FIG. 4.

In some embodiments, the concentration Impurity A, Impurity B, and Unknown C together in the composition after a certain period of shelf life is no more than about 5%, preferably no more than about 4%, more preferably no more than about 3%, more preferably no more than about 2%, more preferably no more than about 1%, and most preferably no more than about 0.5%.

In some embodiments, the concentration of Impurity A in the composition after a certain period of shelf life may be no more than about 2%, preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, and most preferably no more than about 0.1%.

In some embodiments, the concentration of Impurity B in the composition after a certain period of shelf life may be no more than about 2%, preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, and most preferably no more than about 0.1%.

In some embodiments, the concentration of Unknown C in the composition after a certain period of shelf life may be no more than about 2%, preferably no more than about 1.9%, more preferably no more than about 1.8%, more preferably no more than about 1.7%, more preferably no more than about 1.6%, more preferably no more than about 1.5%, more preferably no more than about 1.4%, more preferably no more than about 1.3%, more preferably no more than about 1.2%, more preferably no more than about 1.1%, more preferably no more than about 1%, more preferably no more than about 0.9%, more preferably no more than about 0.8%, more preferably no more than about 0.7%, more preferably no more than about 0.6%, more preferably no more than about 0.5%, more preferably no more than about 0.4%, more preferably no more than about 0.3%, more preferably no more than about 0.2%, and most preferably no more than about 0.1%.

In some embodiments, the presence of Impurity A, Impurity B, and/or Unknown C in the composition may be at least partially related to the presence of oxygen such that reducing oxygen accessible to the composition may reduce the amount of Impurity A, Impurity B, and/or Unknown C present in the composition. In some embodiments, oxygen present in the headspace of a vial containing the composition may be reduced by replacing some or all of the oxygen a gas other than oxygen, preferably an inert gas, thereby at least partially reducing the amount of Impurity A, Impurity B, and/or Unknown C present in the composition. In some embodiments, some or all of the oxygen present in the headspace of a vial containing the composition may be replaced with nitrogen and/or argon.

In some embodiments, other components of the composition may be present at a concentration that reduces the amount of Impurity A, Impurity B, and/or Unknown C present in the composition after a certain period of shelf life and/or reduces the rate of Impurity A, Impurity B, and/or Unknown C formation. In some embodiments, other components of the composition may reduce the amount of Impurity A, Impurity B, and/or Unknown C present in the composition after a certain period of shelf life by interfering with an interaction involving other components of the composition. In some embodiments, other components of the composition may reduce the amount of Impurity A, Impurity B, and/or Unknown C present in the composition after a certain period of shelf life by interfering with an oxidative processes involving epinephrine. In some embodiments, other components of the composition may reduce the presence of Impurity A, Impurity B, and/or Unknown C in the composition after a certain period of shelf life by interacting with a trace metal present in the composition. In some embodiments, the transition metal complexing agent may reduce the amount of Impurity A, Impurity B, and/or Unknown C present in the composition after a certain period of shelf life.

The present invention provides for compositions that may have an extended shelf life. As used throughout this application, the term "shelf life" refers to the length of time that a product may be stored without becoming unfit for medical use. Examples of compositions which are unfit for medical use include, but are not limited to, compositions with unacceptably high impurity levels and/or the presence of physical changes described herein, such as color change and/or the presence of insoluble particles.

In some embodiments, the period of shelf life of the composition may be 1 month, preferably 2 months, more preferably 3 months, more preferably 4 months, more preferably 5 months, more preferably 6 months, more preferably 7 months, more preferably 8 months, more preferably 9 months, more preferably 10 months, more preferably 11 months, more 12 months, preferably 13 months, more preferably 14 months, more preferably 15 months, more preferably 16 months, more preferably 17 months, more preferably 18 months, more preferably 19 months, more preferably 20 months, more preferably 21 months, more preferably 22 months, more preferably 23 months, more preferably 24 months, more preferably 25 months, more preferably 26 months, more preferably 27 months, more preferably 28 months, more preferably 29 months, more preferably 30 months, more preferably 31 months, more preferably 32 months, more preferably 33 months, more preferably 34 months, more preferably 35 months, and most preferably 36 months. In some embodiments, the period of shelf life may vary based on product presentation.

In some embodiments, shelf life may be determined by measuring certain characteristics of the composition that may indicate that the composition is unfit for medical use. In some embodiments, shelf life may be determined by measuring the concentration of impurities in the composition after storage at 25° C. and 60% relative humidity. In some embodiments, shelf life may be determined by measuring the concentration of impurities in the composition after storage at 37° C. and 65% relative humidity.

In some embodiments, shelf life may be determined by measuring the concentration of impurities in the composition using the guidelines as outlined in the ICH Harmonised Tripartite Guideline: Stability Testing of New Drug Substances and Products Q1A(R2), dated Feb. 6, 2003, the disclosure of which is incorporated by reference herein in its entirety.

For example, shelf life may be determined for long term, accelerated, and, where appropriate, intermediate storage conditions by measuring the concentration of impurities after storage in the following conditions, wherein the composition is packaged in a container closure system that is the same as or simulates the packaging proposed for storage and distribution.

| Study | Storage condition | Minimum time period covered |
| --- | --- | --- |
| Long term | 25° C. ± 2° C./ 60% RH ± 5% RH or 30° C. ± 2° C./ 65% RH ± 5% RH | 12 months |
| Intermediate | 30° C. ± 2° C./ 65% RH ± 5% RH | 6 months |
| Accelerated | 40° C. ± 2° C./ 75% RH ± 5% RH | 6 months |

In some embodiments, shelf life may be attributed at least in part to the concentration of impurities in the composition such that the reduction of impurity concentration and/or rate of impurity formation lengthens the composition's shelf life.

The present invention provides for compositions that may have an initial pH which at least partially influences any of the mechanisms described herein. In some embodiments, the initial pH of the composition may be such that the rate of component degradation is minimized. For example, the initial pH of the composition may be such that the rate of formation of D-epinephrine is minimized after a certain period of shelf life. In some embodiments, the initial pH range of the composition may be in the range of about 3.5 and 4.5, preferably in the range of about 3.6 and 4.4, more preferably in the range of about 3.7 and 4.3, more preferably in the range of about 3.8 and 4.2, more preferably in the range of about 3.9 and 4.1, and most preferably about 4.0.

In some embodiments, components of the composition may be selected such that the pH of the composition is within a preferred range. For example, in some embodiments, the pH raising agent may be present in the composition such that the pH of the composition is higher than what it would otherwise be without the presence of the pH raising agent.

In some embodiments, the initial pH may be such that the composition conforms to industry requirements, such as the limit on total acidity imposed by the USP 37-NF 32, S2, monograph.

The present invention also provides for compositions that may resist significant pH change after a certain period of shelf life. In some embodiments, the pH range after a certain period of shelf life of the composition may be in the range of about 2.5 and 5, preferably in the range of about 2.6 and 4.9, more preferably in the range of about 2.7 and 4.8, more preferably in the range of about 2.8 and 4.7, more preferably in the range of about 2.9 and 4.6, more preferably in the range of about 3.0 and 4.5, more preferably in the range of about 3.1 and 4.4, more preferably in the range of about 3.2 and 4.3, more preferably in the range of about 3.3 and 4.2, more preferably in the range of about 3.4 and 4.1, and most preferably in the range of about 3.5 and 4.0.

In some embodiments, components of the composition may be selected such that the pH range after a certain period of shelf life of the composition is within a preferred range. For example, in some embodiments, the pH raising agent may be present in the composition such that the pH range after a certain period of shelf life of the composition is higher than what it would otherwise be without the presence of the pH raising agent.

In some embodiments, the pH range after a certain period of shelf life of the composition may be such that the degradation of components of the composition is reduced. In some embodiments, the pH range after a certain period of shelf life of the composition may be such that the formation of D-epinephrine is reduced. In some embodiments, the pH range after a certain period of shelf life of the composition may be such that the amount of D-epinephrine present in the composition is in a preferred range described herein.

In some embodiments, the pH range after a certain period of shelf life may be such that the degradation of the antioxidant is reduced. For example, for compositions containing sulfites, the conversion of bisulfite to sulfer dioxide may be reduced. The reduction of the conversion of bisulfite to sulfer dioxide may at least in part lead to a higher proportion of antioxidant present in the composition after a certain period of shelf life compared to compositions outside of the preferred pH range.

In some embodiments, the pH range of the composition after a certain period of shelf life does not change significantly from the initial pH of the composition. In some embodiments, the change in pH range may be no more than about 1 unit different than the initial pH of the composition, preferably no more than about 0.9 units, more preferably no more than about 0.8 units, more preferably no more than about 0.7 units, more preferably no more than about 0.6 units, more preferably no more than about 0.5 units, more preferably no more than about 0.4 units, more preferably no more than about 0.3 units, more preferably no more than about 0.2 units, most preferably no more than about 0.1 units. In some embodiments, the pH after a certain period of shelf life may not fall below 3.5.

In some embodiments, the pH range may be such that the composition conforms to the limit on total acidity imposed by the USP 37-NF 32, S2, monograph.

The present invention provides for compositions in single-dose and/or multi-dose formulations. In some embodiments, the composition may be contained in vials. In some embodiments, the vials may comprise clear glass, amber glass, or plastic. In some embodiments, the vials may be in the range of about 0.1 to 500 mL in volume, preferably in the range of about 0.5 to 250 mL, more preferably in the range of about 1 to 100 mL, and most preferably in the range of about 10 to 50 mL. In some embodiments, the composition may exist in a 1 mL vial. In some embodiments, the composition may exist in a 30 mL vial. In some embodiments, the 1 mL vial may be a single-dose formulation. In some embodiments, the 30 mL vial may be a multi-dose formulation. In some embodiments, the same vial may be used for multiple applications of the composition for up to about 10 days after initial use, preferably up to about 15 days, more preferably up to about 30 days, more preferably up to about 45 days, and most preferably up to about 60 days. In some embodiments, the composition may be lyophilized.

In some embodiments, the composition may be contained in an autoinjector.

In some embodiments, the composition may be contained in a pre-filled syringe.

The present invention also provides for methods of making pharmaceutical compositions of the present invention. In some embodiments of carrying out a method of making the present composition, a bulk solution may be produced as follows: water for injections, whose dissolved oxygen content is in an acceptable range as measured by a WFI USP/EP $O_2$ probe, may be added to a manufacturing tank kept under nitrogen pressure. Then, a tonicity regulating agent may be added and mixed. Then, a pH raising agent may be added to the solution while mixing. Then, a metal complexing agent may then be added to the solution while mixing. An antioxidant may then be added while mixing.

In another container equipped with a stir bar, a pH lowering agent may be combined with an active agent. The pH lowering agent and the active agent together may then be stirred using the stir bar in the separate container before the mixture is added to the manufacturing tank under nitrogen.

Then, the separate container may be rinsed with water for injections, whose dissolved oxygen content is in an acceptable range as measured by a WFI USP/EP $O_2$ probe, using a pipet and added to the manufacturing tank. This rinsing step may be repeated 1 to 3 more times. The solution may then mix before the final net weight of the solution is adjusted using water for injections.

The present invention also provides for methods of treating or reducing the symptoms associated with a medical condition, comprising administering to a subject in need thereof the pharmaceutical composition of the present invention.

Examples of conditions to be treated comprise bronchospasm, sensitivity reactions, cardiac arrhythmias, GI and renal hemorrhage, superficial bleeding, premature labor, hypoglycemia, and cardiogenic, hemorrhagic, and traumatic shock. In some embodiments, the present invention provides for methods for reducing the symptoms associated with allergic reactions (Type 1), including anaphylaxis, and/or for the induction and maintenance of mydriasis during intraocular surgery.

Examples of methods of administration comprise subcutaneous, intracameral, intravenous, and intramuscular injection, infusion, intra-arterial administration, intracardiac injection, endotracheal administration, intraosseous administration, oral inhalation, topical administration, and as ophthalmic irrigation.

Unless otherwise noted, all concentrations herein (other than percentage of impurities) are expressed as weight/volume percent (w/v %) of the composition.

The present invention is further described by way of the following non-limiting Examples that are given for illustrative purposes only.

Examples 1-24 represent example compositions according to the present invention.

Example 1

| Ingredient | Concentration (mM) |
| --- | --- |
| Epinephrine | 1-10 |
| Tonicity regulating agent | 75-150 |
| Antioxidant | 1-10 |
| pH lowering agent | 2-11 |
| Transition metal complexing agent | 0.1-15 |
| Water | Fill to final total volume |

Example 2

| Ingredient | Concentration (mM) |
| --- | --- |
| Epinephrine | 4-8 |
| Tonicity regulating agent | 90-140 |
| Antioxidant | 2-6 |
| pH lowering agent | 4-8 |
| Transition metal complexing agent | 0.2-2 |
| Water | Fill to final total volume |

Example 3

| Ingredient | Concentration (mM) |
| --- | --- |
| Epinephrine | 1-10 |
| Sodium Chloride | 75-150 |
| Sodium Metabisulfite | 1-10 |
| Hydrochloric Acid 4% Solution | 2-11 |
| Tetraethylenepentamine | 0.1-15 |
| Water | Fill to final total volume |

Example 4

| Ingredient | Concentration (mM) |
| --- | --- |
| Epinephrine | 1-10 |
| Sodium Chloride | 75-150 |
| Sodium Metabisulfite | 1-10 |
| Hydrochloric Acid 4% Solution | 2-11 |
| Disodium Edetate Dihydrate | 0.1-15 |
| Water | Fill to final total volume |

Example 5

| Ingredient | Concentration (mM) |
| --- | --- |
| Epinephrine | 1-10 |
| Tonicity regulating agent | 75-150 |
| pH raising agent | 10-70 |
| Antioxidant | 1-10 |
| pH lowering agent | 2-11 |
| Water | Fill to final total volume |

Example 6

| Ingredient | Concentration (mM) |
| --- | --- |
| Epinephrine | 4-8 |
| Tonicity regulating agent | 90-140 |
| pH raising agent | 30-50 |
| Antioxidant | 2-6 |
| pH lowering agent | 4-8 |
| Water | Fill to final total volume |

Example 7

| Ingredient | Concentration (mM) |
| --- | --- |
| Epinephrine | 3-11 |
| Sodium Chloride | 80-160 |
| Tartaric Acid | 7-21 |
| Sodium Hydroxide | 15-30 |
| Sodium Metabisulfite | 1-10 |
| Hydrochloric Acid 4% Solution | 1-10 |
| Water | Fill to final total volume |

Example 8

| Ingredient | Concentration (mg/mL) |
| --- | --- |
| Epinephrine | 1-9 |
| Sodium Chloride | 1-10 |
| Tartaric Acid | 2-15 |
| Sodium Hydroxide | 1-5 |
| Sodium Metabisulfite | 1-12 |
| Hydrochloric Acid 4% Solution | 0-6 (mL/mL) |
| Water | Fill to final total volume |

Example 9

| Ingredient | Concentration (mM) |
| --- | --- |
| Epinephrine | 1-15 |
| Sodium Chloride | 75-150 |
| Lactic Acid | 5-25 |
| Sodium Hydroxide | 15-30 |
| Sodium Metabisulfite | 1-10 |
| Hydrochloric Acid 4% Solution | 1-10 |
| Water | Fill to final total volume |

Example 10

| Ingredient | Concentration (mM) |
| --- | --- |
| Epinephrine | 1-10 |
| Tonicity regulating agent | 75-150 |
| pH raising agent | 10-70 |
| Antioxidant | 1-10 |
| pH lowering agent | 2-11 |
| Transition metal complexing agent | 0.1-15 |
| Water | Fill to final total volume |

Example 11

| Ingredient | Concentration (mM) |
| --- | --- |
| Epinephrine | 4-8 |
| Tonicity regulating agent | 90-140 |
| pH raising agent | 30-50 |
| Antioxidant | 2-6 |
| pH lowering agent | 4-8 |
| Transition metal complexing agent | 0.2-2 |
| Water | Fill to final total volume |

Example 12

| Ingredient | Concentration (mM) |
| --- | --- |
| Epinephrine | 3-11 |
| Sodium Chloride | 80-160 |
| Tartaric Acid | 7-21 |
| Sodium Hydroxide | 15-30 |
| Sodium Metabisulfite | 1-10 |
| Hydrochloric Acid 4% Solution | 1-10 |
| Disodium Edetate Dihydrate | 0-5 |
| Water | Fill to final total volume |

Example 13

| Ingredient | Concentration (mM) |
| --- | --- |
| Epinephrine | 1-15 |
| Sodium Chloride | 75-150 |
| Lactic Acid | 5-25 |
| Sodium Hydroxide | 15-30 |
| Sodium Metabisulfite | 1-10 |
| Hydrochloric Acid 4% Solution | 1-10 |
| Disodium Edetate Dihydrate | 0.5-8.5 |
| Water | Fill to final total volume |

Example 14

| Ingredient | Concentration (mM) |
| --- | --- |
| Epinephrine | 1-15 |
| Sodium Chloride | 50-150 |
| Tartaric Acid | 5-20 |
| Sodium Hydroxide | 15-30 |
| Sodium Metabisulfite | 3-18 |
| Hydrochloric Acid 4% Solution | 1-10 |
| Tetraethylenepentamine | 0.5-10.5 |
| Water | Fill to final total volume |

Example 15

| Ingredient | Concentration (mM) |
| --- | --- |
| Epinephrine | 1-10 |
| Tonicity regulating agent | 75-150 |
| pH raising agent | 10-70 |
| Antioxidant | 1-10 |
| Preservative | 10-50 |
| pH lowering agent | 2-11 |
| Transition metal complexing agent | 0.1-15 |
| Water | Fill to final total volume |

Example 16

| Ingredient | Concentration (mM) |
| --- | --- |
| Epinephrine | 4-8 |
| Tonicity regulating agent | 90-140 |
| pH raising agent | 30-50 |
| Antioxidant | 2-6 |

-continued

| Ingredient | Concentration (mM) |
| --- | --- |
| Preservative | 20-40 |
| pH lowering agent | 4-8 |
| Transition metal complexing agent | 0.2-2 |
| Water | Fill to final total volume |

Example 17

| Ingredient | Concentration (mg/mL) |
| --- | --- |
| Epinephrine | 1-10 |
| Sodium Chloride | 4-12 |
| Lactic Acid | 0.5-15 |
| Sodium Hydroxide | 1-5 |
| Sodium Metabisulfite | 0.1-10.1 |
| Chlorobutanol, hydrous | 3-12 |
| Hydrochloric Acid 4% Solution | 0.1-5 (mL/mL) |
| Disodium Edetate Dihydrate | 1-15 |
| Water | Fill to final total volume |

Example 18

| Ingredient | Concentration (mM) |
| --- | --- |
| Epinephrine | 1-15 |
| Sodium Chloride | 50-150 |
| Tartaric Acid | 5-20 |
| Sodium Hydroxide | 15-30 |
| Sodium Metabisulfite | 3-18 |
| Chlorobutanol, hydrous | 10-30 |
| Hydrochloric Acid 4% Solution | 1-10 |
| Tetraethylenepentamine | 0.5-10.5 |
| Water | Fill to final total volume |

Example 19

| Ingredient | Concentration (mM) |
| --- | --- |
| Epinephrine | 0.62 |
| Sodium Chloride | 133.47 |
| Tartaric Acid | 14.99 |
| Sodium Hydroxide | 25.00 |
| Glutathione | 4.88 |
| Hydrochloric Acid | 0.69 |
| Disodium Edetate Dihydrate | 0.54 |
| Water | Fill to final total volume |

Example 20

| Ingredient | Concentration (mg/mL) |
| --- | --- |
| Epinephrine | 0.114 |
| Sodium Chloride | 7.8 |
| Tartaric Acid | 2.25 |
| Sodium Hydroxide | 1 |
| Glutathione | 1.5 |
| Hydrochloric Acid | 0.025 |

-continued

| Ingredient | Concentration (mg/mL) |
| --- | --- |
| Disodium Edetate Dihydrate | 0.2 |
| Water | Fill to final total volume |

Example 21

| Ingredient | Concentration (mM) |
| --- | --- |
| Epinephrine | 0.62 |
| Sodium Chloride | 133.47 |
| Tartaric Acid | 14.99 |
| Sodium Hydroxide | 25.00 |
| Methionine | 4.89 |
| Hydrochloric Acid | 0.69 |
| Disodium Edetate Dihydrate | 0.54 |
| Water | Fill to final total volume |

Example 22

| Ingredient | Concentration (mg/mL) |
| --- | --- |
| Epinephrine | 0.114 |
| Sodium Chloride | 7.8 |
| Tartaric Acid | 2.25 |
| Sodium Hydroxide | 1 |
| Methionine | 0.73 |
| Hydrochloric Acid | 0.025 |
| Disodium Edetate Dihydrate | 0.2 |
| Water | Fill to final total volume |

Example 23

| Ingredient | Concentration (mM) |
| --- | --- |
| Epinephrine | 0.62 |
| Sodium Chloride | 133.47 |
| Tartaric Acid | 14.99 |
| Sodium Hydroxide | 25.00 |
| Ascorbic Acid | 4.83 |
| Hydrochloric Acid | 0.69 |
| Disodium Edetate Dihydrate | 0.54 |
| Water | Fill to final total volume |

Example 24

| Ingredient | Concentration (mg/mL) |
| --- | --- |
| Epinephrine | 0.114 |
| Sodium Chloride | 7.8 |
| Tartaric Acid | 2.25 |
| Sodium Hydroxide | 1 |
| Ascorbic Acid | 0.85 |
| Hydrochloric Acid | 0.025 |
| Disodium Edetate Dihydrate | 0.2 |
| Water | Fill to final total volume |

Example 25

The following study was performed in order to compare the stability of compositions according to the present invention with other epinephrine-containing compositions. In particular, a 1 mL formulation according to Example 19 and a 1 mL formulation according to Comparative Composition 1 (below) were subjected to both accelerated (40° C.) and long term (25° C.) storage conditions for 3 months and 6 months, respectively.

Comparative Composition 1

| Ingredient | Concentration (mg/mL) |
|---|---|
| Epinephrine | 0.114 |
| Sodium Chloride | 7.8 |
| Tartaric Acid | 2.25 |
| Sodium Hydroxide | 1 |
| Sodium Metabisulfite | 0.457 |
| Hydrochloric Acid | 0.025 |
| Disodium Edetate Dihydrate | 0.2 |
| Water | Fill to final total volume |

The total concentration of impurities was determined at various time points during the study. The impurities measured included D-epinephrine, ESA, adrenalone, Impurity A, Impurity B, Unknown C, and adrenochrome sulfonate.

Figure 5:
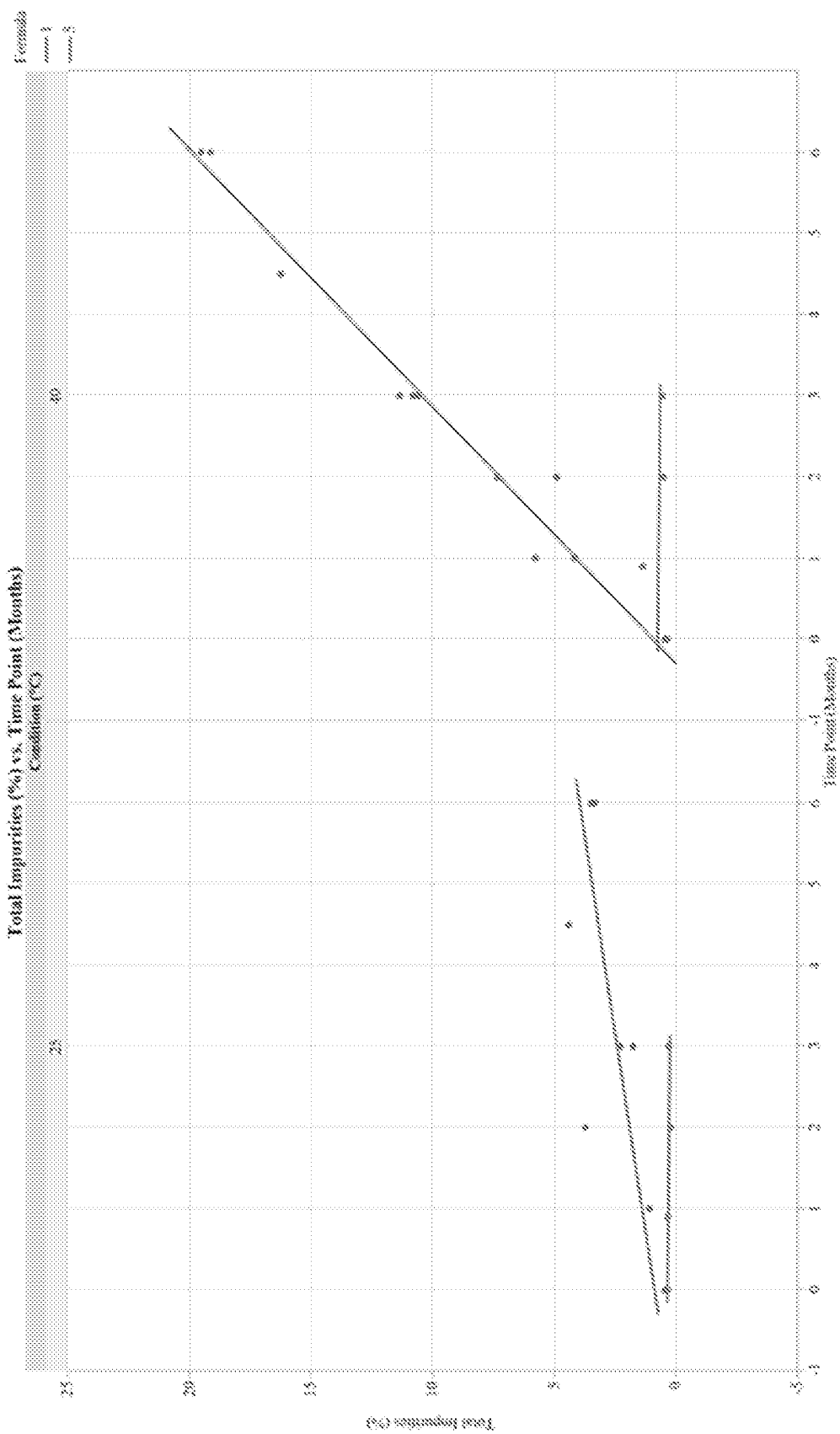
FIG. 5 shows the total concentration of impurities at various time points during the study according to Example 25.

The results of this study for both long term and accelerated storage conditions are shown in FIG. 5. In particular, FIG. 5 shows that the composition according to Example 19 surprisingly shows significantly less impurities after 3 months at both long term and accelerated storage conditions when compared to Comparative Composition 1.

Example 26

In this study, a 1 mL formulation according to Example 19 and a 1 mL formulation according to Comparative Composition 2 (below) were subjected to accelerated (40° C.) and/or long term (25° C.) storage conditions for 3 months.

Comparative Composition 2

| Ingredient | Concentration (mg/mL) |
|---|---|
| Epinephrine | 0.114 |
| Sodium Chloride | 7.8 |
| Tartaric Acid | 2.25 |
| Sodium Hydroxide | 1 |
| Sodium Metabisulfite | 0.2285 |
| Hydrochloric Acid | 0.025 |
| Disodium Edetate Dihydrate | 0.2 |
| Water | Fill to final total volume |

The total concentration of impurities was determined at various time points during the study. The impurities measured included D-epinephrine, ESA, adrenalone, Impurity A, Impurity B, Unknown C, and adrenochrome sulfonate.

Figure 6:
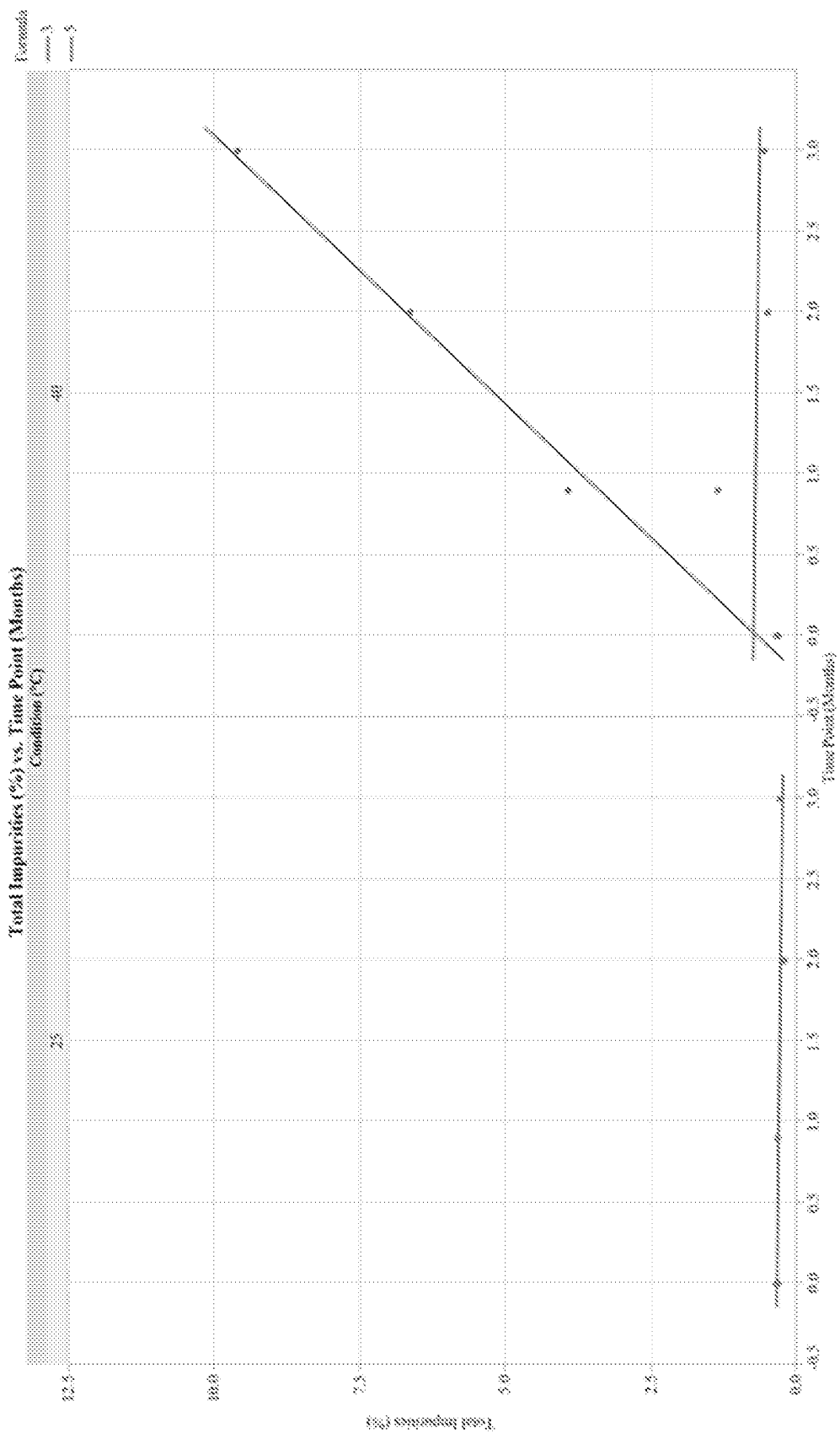
FIG. 6 shows the total concentration of impurities at various time points during the study according to Example 26.

The results of this study for both long term and accelerated storage conditions are shown in FIG. 6. In particular, FIG. 6 shows that the composition according to Example 19 surprisingly shows significantly less impurities after 3 months at accelerated storage conditions when compared to Comparative Composition 2, and a surprisingly low concentration of impurities after 3 months at long term storage conditions.

Example 27

The following is an example procedure for separating and characterizing substances that may be present in pharmaceutical compositions comprising epinephrine. Specifically, this procedure utilizes High Performance Liquid Chromatography (H PLC) to separate certain components. Individual components may then be detected and determined by their UV absorbance response at a wavelength of 280 nm.

The chromatographic conditions utilized in this procedure are as follows:

| Instrument | Agilent 1100 series |
|---|---|
| Column | 4.6 × 150 mm, SeQuant ZIC-HILIC 3.5 µm, 100 Å (EMD Millipore Part No. 1.50444.0001) |
| Column Temperature | 35° C. |
| Flow Rate | 1.0 mL/min |
| Injection Volume | 100 µL |
| Detector | UV Absorbance with a Diode Array Detector |

| Signal (nm) | Bandwidth (nm) | Reference |
|---|---|---|
| 280 | 10 | OFF |
| 292 | 10 | OFF |
| 346 | 10 | OFF |
| 380 | 10 | OFF |

| Run Time | 35 minutes | | |
|---|---|---|---|
| Pump (Gradient) | Time (minutes) | % Mobile Phase A | % Mobile Phase B |
| | 0 | 87 | 13 |
| | 12 | 87 | 13 |
| | 22 | 70 | 30 |
| | 25 | 70 | 30 |
| | 28 | 87 | 13 |
| | 35 | 87 | 13 |

The reagents necessary for this procedure are as follows: water, Milli-Q or equivalent; Formic Acid, 88% ACS Reagent Grade; Ammonium Hydroxide, 6.0 M Reagent Grade or equivalent; Sodium Chloride, ACS Reagent Grade or equivalent; Acetonitrile, HPLC grade or equivalent; and 0.9% Saline Solution.

From these reagents, the following preparations are prepared:
Ammonium Formate Buffer First, 1.5 g of Sodium Chloride is dissolved in 1.0 L of water and then filtered through a 0.45 µm nylon membrane. Then, 5.0 mL of Formic Acid, 88% and 3.0 mL of 6.0 M Ammonium Hydroxide are added and mixed thoroughly. The resulting solution is about 133 mM in Formic Acid and 18 mM in Ammonia with a pH about 2.9.
Mobile Phase A 100 mL of the Ammonium Formate Buffer is mixed with 900 mL of Acetonitrile.
Mobile Phase B 100 mL of the Ammonium Formate Buffer is mixed with 400 mL of water and 500 mL of Acetonitrile.
Stock Standard Solution First, 45 mg of USP Epinephrine Bitartrate Reference Standard or a qualified In-House Reference Standard is accurately weighed and transferred into a 25 mL amber volumetric flask. This is then dissolved in and diluted to volume with the Ammonium Formate Buffer. The solution is mixed by inverting and shaking the volumetric flask at least ten times.
Intermediate Standard Solution First, 2.0 mL of the Stock Standard Solution is pipetted into a 200 mL volumetric flask. The solution is then diluted to volume with the Ammonium Formate Buffer. It is mixed by inverting and shaking the volumetric flask at least ten times.

Working Standard Preparation

First, 5.0 mL of the Intermediate Standard Solution is pipetted into a volumetric flask. Then, 15.0 mL of Acetonitrile is pipetted into the same volumetric flask. (The volume is not diluted). The solution is mixed thoroughly. (Standard Preparations stored at room temperature protected from light are stable for 48 hours.)

Blank Preparation #1

First, 5.0 mL of the Ammonium Formate Buffer is pipetted into a volumetric flask. Then, 15.0 mL of Acetonitrile is pipetted into the same volumetric flask. (The volume is not diluted.) The preparation is mixed thoroughly.

Blank Preparation #2

First, 5.0 mL of 0.9% Saline is pipetted into a volumetric flask. Then, 15.0 mL of Acetonitrile is pipetted into the same volumetric flask. (The volume is not diluted.) The preparation is mixed thoroughly.

Photodegraded Solution

In a clean, clear 2 L glass bottle, 800 mL of water is added. Then, about 6.147 g of NaCl is added followed by about 2.251 g of Tartaric Acid. The components are mixed to dissolve. 6.25 mL of 5.0 N NaOH is then added and mixed well. Then, about 1.425 g of Sodium Metabisulfite is added. About 1.1334 g of Epinephrine is then diluted with 6.6 mL of 1.0 N HCl and quantitatively transferred to the 2 L glass bottle. The solution is then diluted to a final volume of 1 L and exposed to continuous light in the hood for 12 days, or in a photostability light chamber for two days.

EpiHILIC IMS (Impurity Marker Solution)

500 mL of the photodegraded solution is added to a 500 mL clear glass bottle. Then, 6.0 mL of 1.0 N HCl is added and mixed well. About 9.5 mg of ESA is added and mixed to dissolve. About 5.6 mg of Adrenochrome is then added and mixed to dissolve. Then, exactly 10 mL of this solution is withdrawn and about 4.7 mg of Adrenalone is added. It is mixed to dissolve. 0.8 mL of the Adrenalone stock is then added back to the bulk mixture and mixed to dissolve. The remaining Adrenalone stock is discarded. The solution is mixed well and transferred to individual amber Autosampler vials. The vials are stored refrigerated or frozen.

Intermediate IMS 5.0 mL of the EpiHILIC IMS is pipetted into a 50 mL volumetric flask and diluted to volume with 0.9% Saline Solution.

Working IMS

One volume of the Intermediate IMS is diluted with about 3 volumes of Acetonitrile.

Test samples may then be injected. The Working Standard Preparations should be injected after every 4 sample injections or less and the bracketing standard peak areas should be averaged for use in the calculations. The chromatograms and the Epinephrine and Related Substance peak areas should be measured using the outlined parameters. The Epinephrine Bitartrate peak area in each ongoing standard must be 90.0-110.0% of the average area of Epinephrine Bitartrate in n=5 injections of Working Standard Preparation injections.

After the completion of each chromatographic run, the column is washed as follows: 20 column volumes of deionized water; 30 column volumes of 0.5 M NaCl; 30 column volumes of deionized water; 20 column volumes of acetonitrile/water (50:50, v/v); 20 column volumes of acetonitrile; and 20 column volumes of acetonitrile/water (50:50, v/v).

For identification, the retention time of the main peak in the chromatogram of the Sample Preparation ($t_{sample}$) is compared with the prior injection of the Working Standard Preparation ($t_{std}$). For a positive test, $R_r$ should be 0.98 to 1.02, wherein $R_r$ is ($t_{sample}/t_{std}$).

The following information can then be calculated:

$$\text{Assay (mg/mL)} = (A_E/A_s) \times (S/25) \times (2/200) \times (P/100) \times (183.20/333.29)$$

$$\text{Assay (\% LabelClaim)} = (\text{Assay (mg/mL)}/0.1 \text{ nm/mL}) \times 100\%$$

$$\text{\% Related Substances (RS)} = (A_{RS}/A_s) \times \text{RRM} \times (S/25) \times (2/200) \times (P/100) \times (183.20/333.29) \times (100\%/0.1 \text{ mg/ml})$$

where $A_E$ is the Epinephrine peak area for the Sample Preparation; $A_s$ is the average Epinephrine peak area for the Bracketing Working Standard injections; S is the weight in milligrams of Epinephrine Bitartrate in the Stock Standard Preparation; P is the Purity of Epinephrine Bitartrate in the Stock Standard Preparation expressed as a percentage; 183.20 is the molecular weight of Epinephrine; 333.29 is the molecular weight of Epinephrine Bitartrate; 0.1 mg/mL is the Label Claim for the Adrenalin® syringe; ARS is the peak area for related substance in the Sample Preparation integrated at the detection wavelength in the below table; As is the average Epinephrine peak area for the Bracketing Standard injections, and RRF is the Relative Response Multiplier from the below table. Specifically, the below table shows the Relative Retention Time (that is, the time it takes for each individual substances to elute from the HPLC column, or RRT) and RRM for several specified and unspecified related substances:

| Substance | Approx. RRT | Detection Wavelength | Relative Response Multiplier (RRM) |
|---|---|---|---|
| Epinephrine | 1.00 | 280 | |
| Adrenalone | 0.62 | 280 | 0.29 |
| ESA | 1.91 | 280 | 1.37 |
| Impurity B | 0.57 | 292 | 1.09 |
| Impurity A | 2.06 | 292 | 1.09 |
| Adrenochrome Sulfonate (AdrS) | 1.29 | 346 | 0.35 |
| Unk C | 1.84 | 380 | 1 |
| Unspecified | | 280 | 1 |

Example 28

The following studies were performed in order to compare the stability of certain epinephrine-containing compositions. Specifically, 18 samples (Samples A-P) were subjected to accelerated (40° C.) and/or long term (25° C.) storage conditions for up to 6 months. Each of the 18 samples consisted of one of the 6 formulations below.

| Formulation 1 | | |
|---|---|---|
| | Concentration | |
| Ingredient | mg/mL | mM |
| Epinephrine | 0.114 | 0.62 |
| Sodium Chloride | 7.8 | 133.47 |
| Tartaric Acid | 2.25 | 14.99 |
| Sodium Hydroxide | 1 | 25.00 |
| Sodium Metabisulfite | 0.457 | 4.81 |
| Hydrochloric Acid | 0.025 | 0.69 |
| Disodium Edetate Dihydrate | 0.2 | 0.54 |
| Water for Injection | QS to 1 mL | N/A |

Formulation 2

| Ingredient | Concentration mg/mL | mM |
|---|---|---|
| Epinephrine | 0.114 | 0.62 |
| Sodium Chloride | 9 | 154.00 |
| Tartaric Acid | 0.225 | 1.50 |
| Sodium Hydroxide | 0.1 | 2.50 |
| Sodium Metabisulfite | 0.0457 | 0.48 |
| Hydrochloric Acid | 0.025 | 0.69 |
| Disodium Edetate Dihydrate | 0.02 | 0.05 |
| Water for Injection | QS to 1 mL | N/A |

Formulation 3

| Ingredient | Concentration mg/mL | mM |
|---|---|---|
| Epinephrine | 0.114 | 0.62 |
| Sodium Chloride | 7.8 | 133.47 |
| Tartaric Acid | 2.25 | 14.99 |
| Sodium Hydroxide | 1 | 25.00 |
| Sodium Metabisulfite | 0.2285 | 2.40 |
| Hydrochloric Acid | 0.025 | 0.69 |
| Disodium Edetate Dihydrate | 0.2 | 0.54 |
| Water for Injection | QS to 1 mL | N/A |

Formulation 4

| Ingredient | Concentration mg/mL | mM |
|---|---|---|
| Epinephrine | 0.114 | 0.62 |
| Sodium Chloride | 7.8 | 133.47 |
| Tartaric Acid | 2.25 | 14.99 |
| Sodium Hydroxide | 1 | 25.00 |
| Ascorbic Acid | 0.85 | 4.83 |
| Hydrochloric Acid | 0.025 | 0.69 |
| Disodium Edetate Dihydrate | 0.2 | 0.54 |
| Water for Injection | QS to 1 mL | N/A |

Formulation 5

| Ingredient | Concentration mg/mL | mM |
|---|---|---|
| Epinephrine | 0.114 | 0.62 |
| Sodium Chloride | 7.8 | 133.47 |
| Tartaric Acid | 2.25 | 14.99 |
| Sodium Hydroxide | 1 | 25.00 |
| Glutathione | 1.5 | 4.88 |
| Hydrochloric Acid | 0.025 | 0.69 |
| Disodium Edetate Dihydrate | 0.2 | 0.54 |
| Water for Injection | QS to 1 mL | N/A |

Formulation 6

| Ingredient | Concentration mg/mL | mM |
|---|---|---|
| Epinephrine | 0.114 | 0.62 |
| Sodium Chloride | 7.8 | 133.47 |
| Tartaric Acid | 2.25 | 14.99 |
| Sodium Hydroxide | 1 | 25.00 |
| Methionine | 0.73 | 4.89 |
| Hydrochloric Acid | 0.025 | 0.69 |
| Disodium Edetate Dihydrate | 0.2 | 0.54 |
| Water for Injection | QS to 1 mL | N/A |

Table 8 shows certain physical attributes of the compositions at various time points during the study, including pH and color. (In Table 8, "C/C" denotes "clear/colorless.")

TABLE 8

Physical attributes of epinephrine-containing formulations at various temperatures and time points

| Sample | Formulation | Condition (° C.) | Time Point (Months) | Description | pH |
|---|---|---|---|---|---|
| A | 1 | 25 | 0 | C/C | 4.32 |
| A | 1 | 25 | 3 | C/C | 4.23 |
| A | 1 | 25 | 3 | C/C | 4.23 |
| A | 1 | 25 | 6 | C/C | 4.28 |
| A | 1 | 25 | 6 | C/C | 4.25 |
| A | 1 | 40 | 0 | C/C | 4.32 |
| A | 1 | 40 | 1 | C/C | 4.30 |
| A | 1 | 40 | 2 | C/C | 4.26 |
| A | 1 | 40 | 3 | C/C | 4.24 |
| A | 1 | 40 | 3 | C/C | 4.22 |
| A | 1 | 40 | 6 | C/C | 4.26 |
| A | 1 | 40 | 6 | C/C | 4.26 |
| B | 2 | 25 | 0 | C/C | 4.33 |
| B | 2 | 25 | 3 | C/C | 4.25 |
| B | 2 | 25 | 3 | C/C | 4.28 |
| B | 2 | 25 | 6 | C/C | 4.30 |
| B | 2 | 25 | 6 | C/C | 4.31 |
| B | 2 | 40 | 0 | C/C | 4.33 |
| B | 2 | 40 | 1 | C/C | 4.29 |
| B | 2 | 40 | 2 | C/C | 4.32 |
| B | 2 | 40 | 3 | C/C | 4.34 |
| B | 2 | 40 | 3 | C/C | 4.32 |
| B | 2 | 40 | 6 | C/C | 4.28 |
| B | 2 | 40 | 6 | C/C | 4.16 |
| C | 3 | 25 | 0 | C/C | 4.34 |
| C | 3 | 40 | 0 | C/C | 4.34 |
| C | 3 | 40 | 0.9 | C/C | 4.30 |
| C | 3 | 40 | 2 | C/C | 4.34 |
| C | 3 | 40 | 3 | C/C | 4.18 |
| C | 3 | 40 | 6 | C/C | 4.27 |
| D | 3 | 25 | 0 | C/C | 4.34 |
| D | 3 | 25 | 0.9 | C/C | 4.29 |
| D | 3 | 25 | 2 | C/C | 4.32 |
| D | 3 | 25 | 3 | C/C | 4.28 |
| D | 3 | 25 | 4.5 | C/C | 4.35 |
| D | 3 | 25 | 6 | C/C | 4.36 |
| D | 3 | 40 | 0 | C/C | 4.34 |
| D | 3 | 40 | 0.9 | C/C | 4.27 |
| D | 3 | 40 | 2 | C/C | 4.31 |
| D | 3 | 40 | 3 | C/C | 4.24 |
| D | 3 | 40 | 4.5 | C/C | 4.39 |
| D | 3 | 40 | 6 | C/C | 4.65 |
| E | 3 | 25 | 0 | C/C | 4.34 |
| E | 3 | 25 | 0.9 | C/C | 4.33 |
| E | 3 | 25 | 2 | C/C | 4.34 |
| E | 3 | 25 | 3 | C/C | 4.32 |
| E | 3 | 25 | 4.5 | C/C | 4.34 |
| E | 3 | 25 | 6 | C/C | 4.31 |
| E | 3 | 40 | 0 | C/C | 4.34 |
| E | 3 | 40 | 0.9 | C/C | 4.31 |
| E | 3 | 40 | 2 | C/C | 4.30 |
| E | 3 | 40 | 3 | C/C | 4.26 |
| E | 3 | 40 | 4.5 | C/C | 4.35 |

TABLE 8-continued

Physical attributes of epinephrine-containing formulations at various temperatures and time points

| Sample | Formulation | Condition (° C.) | Time Point (Months) | Description | pH |
|---|---|---|---|---|---|
| E | 3 | 40 | 6 | C/C | 4.27 |
| F | 3 | 25 | 0 | C/C | 4.34 |
| F | 3 | 25 | 0.9 | C/C | 4.37 |
| F | 3 | 25 | 2 | C/C | 4.37 |
| F | 3 | 25 | 3 | C/C | 4.36 |
| F | 3 | 25 | 4.5 | C/C | 4.34 |
| F | 3 | 25 | 6 | C/C | 4.35 |
| F | 3 | 40 | 0 | C/C | 4.34 |
| F | 3 | 40 | 0.9 | C/C | 4.35 |
| F | 3 | 40 | 2 | C/C | 4.36 |
| F | 3 | 40 | 3 | C/C | 4.32 |
| F | 3 | 40 | 4.5 | C/C | 4.41 |
| F | 3 | 40 | 6 | C/C | 4.36 |
| G | 3 | 25 | 0 | C/C | 4.34 |
| G | 3 | 25 | 0.9 | C/C | 4.35 |
| G | 3 | 25 | 2 | C/C | 4.37 |
| G | 3 | 25 | 3 | C/C | 4.37 |
| G | 3 | 25 | 4.5 | C/C | 4.31 |
| G | 3 | 25 | 6 | C/C | 4.33 |
| G | 3 | 40 | 0 | C/C | 4.34 |
| G | 3 | 40 | 0.9 | C/C | 4.35 |
| G | 3 | 40 | 2 | C/C | 4.36 |
| G | 3 | 40 | 3 | C/C | 4.33 |
| G | 3 | 40 | 4.5 | C/C | 4.44 |
| G | 3 | 40 | 6 | C/C | 4.33 |
| H | 4 | 25 | 0 | C/C | 4.10 |
| H | 4 | 25 | 0.9 | C/C | 4.11 |
| H | 4 | 25 | 2 | C/C | 4.10 |
| H | 4 | 25 | 3 | Pale Yellow | 4.12 |
| H | 4 | 25 | 4.5 | Yellow | 4.10 |
| H | 4 | 25 | 6 | Yellow | 4.12 |
| H | 4 | 40 | 0 | C/C | 4.10 |
| H | 4 | 40 | 0.9 | C/C | 4.09 |
| H | 4 | 40 | 2 | Pale Yellow | 4.13 |
| H | 4 | 40 | 3 | Yellow | 4.04 |
| H | 4 | 40 | 4.5 | Yellow | 4.09 |
| H | 4 | 40 | 6 | Dark Yellow | 4.13 |
| I | 5 | 25 | 0 | C/C | 4.11 |
| I | 5 | 25 | 0.9 | C/C | 4.11 |
| I | 5 | 25 | 2 | C/C | 4.11 |
| I | 5 | 25 | 3 | C/C | 4.12 |
| I | 5 | 25 | 4.5 | C/C | 4.12 |
| I | 5 | 25 | 6 | C/C | 4.11 |
| I | 5 | 40 | 0 | C/C | 4.11 |
| I | 5 | 40 | 0.9 | C/C | 4.12 |
| I | 5 | 40 | 2 | C/C | 4.12 |
| I | 5 | 40 | 3 | C/C | 4.07 |
| I | 5 | 40 | 4.5 | C/C | 4.11 |
| I | 5 | 40 | 6 | C/C | 4.11 |
| J | 6 | 25 | 0 | C/C | 4.29 |
| J | 6 | 25 | 0.9 | C/C | — |
| J | 6 | 40 | 0 | C/C | 4.29 |
| J | 6 | 40 | 0.9 | Brown | — |
| K | 2 | 25 | 0 | C/C | 4.29 |
| K | 2 | 25 | 1 | C/C | 4.35 |
| K | 2 | 25 | 2 | C/C | 4.32 |
| K | 2 | 25 | 3 | C/C | 4.43 |
| K | 2 | 40 | 0 | C/C | 4.29 |
| K | 2 | 40 | 1 | C/C | 4.36 |
| K | 2 | 40 | 2 | C/C | 4.39 |
| K | 2 | 40 | 3 | C/C | 4.47 |
| L | 2 | 25 | 0 | C/C | 4.38 |
| L | 2 | 25 | 1 | C/C | 4.35 |
| L | 2 | 25 | 2 | C/C | 4.36 |
| L | 2 | 25 | 3 | C/C | 4.39 |
| L | 2 | 40 | 0 | C/C | 4.38 |
| L | 2 | 40 | 1 | C/C | 4.35 |
| L | 2 | 40 | 2 | C/C | 4.37 |
| L | 2 | 40 | 3 | C/C | 4.51 |
| M | 1 | 25 | 0 | C/C | 4.36 |
| M | 1 | 25 | 1 | C/C | 4.39 |
| M | 1 | 25 | 2 | C/C | 4.29 |
| M | 1 | 25 | 3 | C/C | 4.25 |
| M | 1 | 25 | 4.5 | C/C | 4.32 |
| M | 1 | 25 | 6 | C/C | 4.30 |
| M | 1 | 40 | 0 | C/C | 4.36 |
| M | 1 | 40 | 1 | C/C | 4.34 |
| M | 1 | 40 | 2 | C/C | 4.30 |
| M | 1 | 40 | 3 | C/C | 4.26 |
| M | 1 | 40 | 4.5 | C/C | 4.29 |
| M | 1 | 40 | 6 | C/C | 4.26 |
| N | 1 | 25 | 0 | C/C | 4.34 |
| N | 1 | 25 | 1 | C/C | 4.39 |
| N | 1 | 25 | 2 | C/C | 4.15 |
| N | 1 | 25 | 4.5 | C/C | 4.26 |
| N | 1 | 25 | 6 | C/C | 4.23 |
| N | 1 | 25 | 6 | C/C | 4.22 |
| N | 1 | 40 | 0 | C/C | 4.34 |
| N | 1 | 40 | 1 | C/C | 4.33 |
| N | 1 | 40 | 2 | C/C | 4.17 |
| N | 1 | 40 | 3 | C/C | 4.19 |
| N | 1 | 40 | 4.5 | C/C | 4.21 |
| N | 1 | 40 | 6 | C/C | 4.16 |
| N | 1 | 40 | 6 | C/C | 4.16 |
| O | 2 | 25 | 0 | C/C | 4.35 |
| O | 2 | 25 | 1 | C/C | 4.38 |
| O | 2 | 25 | 2 | C/C | 4.33 |
| O | 2 | 25 | 3 | C/C | — |
| O | 2 | 40 | 0 | C/C | 4.35 |
| O | 2 | 40 | 1 | C/C | 4.34 |
| O | 2 | 40 | 2 | C/C | 4.26 |
| O | 2 | 40 | 3 | Brown | — |
| P | 2 | 25 | 0 | C/C | 4.33 |
| P | 2 | 25 | 1 | C/C | 4.36 |
| P | 2 | 25 | 2 | C/C | 4.12 |
| P | 2 | 25 | 4.5 | C/C | 4.24 |
| P | 2 | 25 | 6 | C/C | 4.22 |
| P | 2 | 25 | 6 | C/C | 4.23 |
| P | 2 | 40 | 0 | C/C | 4.33 |
| P | 2 | 40 | 1 | C/C | 4.32 |
| P | 2 | 40 | 2 | C/C | 4.06 |
| P | 2 | 40 | 3 | C/C | 4.21 |
| P | 2 | 40 | 4.5 | C/C | 4.25 |
| P | 2 | 40 | 6 | C/C | 4.20 |
| P | 2 | 40 | 6 | C/C | 4.18 |

Table 9 shows the concentration of D-epinephrine and L-epinephrine in the samples compared with assay values at various time points during the study. In Table 9, "assay" is defined as the sum of D-epinephrine and epinephrine, that is, the concentration of total epinephrine. In addition, in Tables 9-12, "ND" denotes "not determined," that is, a value that is below the limit of detection by the detection method. The data shown in Tables 9-12 were obtained using the HPLC method outlined in Example 27.

TABLE 9

D-epinephrine and L-epinephrine in epinephrine-containing formulations at various temperatures and time points

| Sample | Condition (° C.) | Time Point (Months) | D-Epinephrine (%) | L-Epinephrine (mg/mL) | Assay (mg/mL) |
|---|---|---|---|---|---|
| A | 25 | 0 | 0.32 | 0.103 | 0.103 |
| A | 25 | 3 | 0.28 | 0.121 | 0.122 |
| A | 25 | 3 | 0.27 | 0.121 | 0.122 |
| A | 25 | 6 | 0.31 | 0.113 | 0.114 |
| A | 25 | 6 | 0.34 | 0.113 | 0.114 |
| A | 40 | 0 | 0.32 | 0.103 | 0.103 |
| A | 40 | 1 | 0.18 | 0.118 | 0.118 |
| A | 40 | 2 | 0.41 | 0.114 | 0.114 |
| A | 40 | 3 | 0.40 | 0.112 | 0.113 |
| A | 40 | 3 | 0.39 | 0.112 | 0.113 |

TABLE 9-continued

D-epinephrine and L-epinephrine in epinephrine-containing formulations at various temperatures and time points

| Sample | Condition (° C.) | Time Point (Months) | D-Epinephrine (%) | L-Epinephrine (mg/mL) | Assay (mg/mL) |
|---|---|---|---|---|---|
| A | 40 | 6 | 0.61 | 0.101 | 0.102 |
| A | 40 | 6 | 0.60 | 0.101 | 0.102 |
| B | 25 | 0 | 0.40 | 0.123 | 0.123 |
| B | 25 | 3 | 0.36 | 0.121 | 0.122 |
| B | 25 | 3 | 0.35 | 0.120 | 0.121 |
| B | 25 | 6 | 0.55 | 0.116 | 0.117 |
| B | 25 | 6 | 0.54 | 0.116 | 0.117 |
| B | 40 | 0 | 0.40 | 0.123 | 0.123 |
| B | 40 | 1 | 0.49 | 0.118 | 0.123 |
| B | 40 | 2 | 0.81 | 0.115 | 0.116 |
| B | 40 | 3 | 1.05 | 0.114 | 0.116 |
| B | 40 | 3 | 1.62 | 0.114 | 0.116 |
| B | 40 | 6 | 2.18 | 0.107 | 0.110 |
| B | 40 | 6 | 0.21 | 0.109 | 0.110 |
| C | 25 | 0 | 0.31 | 0.121 | 0.121 |
| C | 40 | 0 | 0.31 | 0.121 | 0.121 |
| C | 40 | 0.9 | 0.27 | 0.117 | 0.118 |
| C | 40 | 2 | 0.38 | 0.119 | 0.119 |
| C | 40 | 3 | 0.42 | 0.114 | 0.115 |
| C | 40 | 6 | 0.54 | 0.107 | 0.108 |
| D | 25 | 0 | 0.31 | 0.121 | 0.121 |
| D | 25 | 0.9 | 0.35 | 0.120 | 0.121 |
| D | 25 | 2 | 0.31 | 0.125 | 0.125 |
| D | 25 | 3 | 0.30 | 0.126 | 0.127 |
| D | 25 | 4.5 | 0.32 | 0.119 | 0.120 |
| D | 25 | 6 | 0.30 | 0.125 | 0.126 |
| D | 40 | 0 | 0.31 | 0.121 | 0.121 |
| D | 40 | 0.9 | 0.42 | 0.121 | 0.122 |
| D | 40 | 2 | 0.76 | 0.123 | 0.135 |
| D | 40 | 3 | 0.89 | 0.139 | 0.140 |
| D | 40 | 4.5 | 1.09 | 0.115 | 0.117 |
| D | 40 | 6 | 1.70 | 0.144 | 0.146 |
| E | 25 | 0 | 0.31 | 0.121 | 0.121 |
| E | 25 | 0.9 | 0.40 | 0.116 | 0.117 |
| E | 25 | 2 | 0.26 | 0.122 | 0.122 |
| E | 25 | 3 | 0.27 | 0.119 | 0.120 |
| E | 25 | 4.5 | 0.31 | 0.117 | 0.118 |
| E | 25 | 6 | 0.24 | 0.119 | 0.120 |
| E | 40 | 0 | 0.31 | 0.121 | 0.121 |
| E | 40 | 0.9 | 0.38 | 0.113 | 0.114 |
| E | 40 | 2 | 0.41 | 0.119 | 0.119 |
| E | 40 | 3 | 0.44 | 0.111 | 0.112 |
| E | 40 | 4.5 | 0.58 | 0.104 | 0.105 |
| E | 40 | 6 | 0.63 | 0.104 | 0.105 |
| F | 25 | 0 | 0.31 | 0.121 | 0.121 |
| F | 25 | 0.9 | 0.33 | 0.116 | 0.117 |
| F | 25 | 2 | 0.29 | 0.122 | 0.122 |
| F | 25 | 3 | 0.27 | 0.120 | 0.121 |
| F | 25 | 4.5 | 0.31 | 0.116 | 0.117 |
| F | 25 | 6 | 0.25 | 0.120 | 0.121 |
| F | 40 | 0 | 0.31 | 0.121 | 0.121 |
| F | 40 | 0.9 | 0.37 | 0.114 | 0.115 |
| F | 40 | 2 | 0.39 | 0.120 | 0.120 |
| F | 40 | 3 | 0.42 | 0.113 | 0.114 |
| F | 40 | 4.5 | 0.54 | 0.106 | 0.107 |
| F | 40 | 6 | 0.55 | 0.108 | 0.109 |
| G | 25 | 0 | 0.31 | 0.121 | 0.121 |
| G | 25 | 0.9 | 0.33 | 0.115 | 0.116 |
| G | 25 | 2 | 0.29 | 0.122 | 0.122 |
| G | 25 | 3 | 0.26 | 0.119 | 0.120 |
| G | 25 | 4.5 | 0.37 | 0.116 | 0.117 |
| G | 25 | 6 | 0.24 | 0.120 | 0.121 |
| G | 40 | 0 | 0.31 | 0.121 | 0.121 |
| G | 40 | 0.9 | 0.38 | 0.113 | 0.114 |
| G | 40 | 2 | 0.40 | 0.119 | 0.119 |
| G | 40 | 3 | 0.44 | 0.111 | 0.112 |
| G | 40 | 4.5 | 0.59 | 0.104 | 0.105 |
| G | 40 | 6 | 0.58 | 0.105 | 0.106 |
| H | 25 | 0 | 0.31 | 0.118 | 0.118 |
| H | 25 | 0.9 | 2.09 | 0.105 | 0.108 |
| H | 25 | 2 | 2.01 | 0.110 | 0.112 |
| H | 25 | 3 | 0.34 | 0.109 | 0.110 |
| H | 25 | 4.5 | 0.46 | 0.109 | 0.110 |
| H | 25 | 6 | 0.70 | 0.115 | 0.116 |
| H | 40 | 0 | 0.31 | 0.118 | 0.118 |
| H | 40 | 0.9 | 1.06 | 0.104 | 0.106 |
| H | 40 | 2 | 0.58 | 0.109 | 0.108 |
| H | 40 | 3 | 0.98 | 0.102 | 0.103 |
| H | 40 | 4.5 | 0.69 | 0.993 | 0.100 |
| H | 40 | 6 | 1.29 | 0.103 | 0.105 |
| I | 25 | 0 | 0.33 | 0.119 | 0.119 |
| I | 25 | 0.9 | 0.31 | 0.119 | 0.120 |
| I | 25 | 2 | 0.20 | 0.119 | 0.119 |
| I | 25 | 3 | 0.26 | 0.119 | 0.120 |
| I | 25 | 4.5 | 0.36 | 0.117 | 0.118 |
| I | 25 | 6 | 0.72 | 0.123 | 0.123 |
| I | 40 | 0 | 0.33 | 0.119 | 0.119 |
| I | 40 | 0.9 | 0.30 | 0.115 | 0.116 |
| I | 40 | 2 | 0.08 | 0.118 | 0.118 |
| I | 40 | 3 | 0.26 | 0.112 | 0.113 |
| I | 40 | 4.5 | 3.22 | 0.103 | 0.107 |
| I | 40 | 6 | 4.56 | 0.109 | 0.109 |
| J | 25 | 0 | 0.33 | 0.118 | 0.118 |
| J | 25 | 0.9 | 0.40 | 0.116 | 0.117 |
| J | 40 | 0 | 0.33 | 0.118 | 0.118 |
| J | 40 | 0.9 | — | — | — |
| K | 25 | 0 | 0.29 | 0.121 | 0.121 |
| K | 25 | 1 | 0.31 | 0.118 | 0.119 |
| K | 25 | 2 | 0.79 | 0.118 | 0.119 |
| K | 25 | 3 | 0.98 | 0.117 | 0.118 |
| K | 40 | 0 | 0.29 | 0.121 | 0.121 |
| K | 40 | 1 | 0.47 | 0.119 | 0.120 |
| K | 40 | 2 | 0.35 | 0.114 | 0.115 |
| K | 40 | 3 | 0.38 | 0.114 | 0.115 |
| L | 25 | 0 | 0.29 | 0.121 | 0.121 |
| L | 25 | 1 | 0.43 | 0.120 | 0.121 |
| L | 25 | 2 | 0.76 | 0.119 | 0.120 |
| L | 25 | 3 | 1.03 | 0.117 | 0.119 |
| L | 40 | 0 | 0.29 | 0.121 | 0.121 |
| L | 40 | 1 | 0.45 | 0.118 | 0.119 |
| L | 40 | 2 | 0.36 | 0.114 | 0.115 |
| L | 40 | 3 | 0.38 | 0.113 | 0.114 |
| M | 25 | 0 | 0.39 | 0.122 | 0.122 |
| M | 25 | 1 | 0.39 | 0.122 | 0.122 |
| M | 25 | 2 | 0.16 | 0.120 | 0.120 |
| M | 25 | 3 | 0.38 | 0.116 | 0.117 |
| M | 25 | 4.5 | 0.31 | 0.122 | 0.122 |
| M | 25 | 6 | 0.30 | 0.119 | 0.120 |
| M | 40 | 0 | 0.39 | 0.122 | 0.122 |
| M | 40 | 1 | 0.42 | 0.119 | 0.119 |
| M | 40 | 2 | 0.23 | 0.116 | 0.116 |
| M | 40 | 3 | 0.55 | 0.108 | 0.109 |
| M | 40 | 4.5 | 0.77 | 0.105 | 0.106 |
| M | 40 | 6 | 2.00 | 0.096 | 0.098 |
| N | 25 | 0 | 0.39 | 0.124 | 0.124 |
| N | 25 | 1 | 0.38 | 0.121 | 0.121 |
| N | 25 | 2 | 0.15 | 0.119 | 0.119 |
| N | 25 | 4.5 | 0.30 | 0.123 | 0.123 |
| N | 25 | 6 | 0.28 | 0.118 | 0.119 |
| N | 25 | 6 | 0.28 | 0.117 | 0.118 |
| N | 40 | 0 | 0.39 | 0.124 | 0.124 |
| N | 40 | 1 | 0.42 | 0.119 | 0.119 |
| N | 40 | 2 | 0.60 | 0.120 | 0.121 |
| N | 40 | 3 | 0.47 | 0.107 | 0.108 |
| N | 40 | 4.5 | 0.52 | 0.110 | 0.111 |
| N | 40 | 6 | 0.53 | 0.104 | 0.105 |
| N | 40 | 6 | 0.54 | 0.105 | 0.106 |
| O | 25 | 0 | 0.38 | 0.123 | 0.123 |
| O | 25 | 1 | 0.40 | 0.124 | 0.124 |
| O | 25 | 2 | 0.18 | 0.123 | 0.123 |
| O | 25 | 3 | — | — | — |
| O | 40 | 0 | 0.38 | 0.123 | 0.123 |
| O | 40 | 1 | 0.70 | 0.120 | 0.121 |
| O | 40 | 2 | 0.86 | 0.118 | 0.119 |
| O | 40 | 3 | — | — | — |
| P | 25 | 0 | 0.39 | 0.124 | 0.124 |

TABLE 9-continued

D-epinephrine and L-epinephrine in epinephrine-containing
formulations at various temperatures and time points

| Sample | Condition (° C.) | Time Point (Months) | D-Epinephrine (%) | L-Epinephrine (mg/mL) | Assay (mg/mL) |
|---|---|---|---|---|---|
| P | 25 | 1 | 0.42 | 0.124 | 0.124 |
| P | 25 | 2 | 0.22 | 0.123 | 0.124 |
| P | 25 | 4.5 | 0.43 | 0.124 | 0.124 |
| P | 25 | 6 | 0.41 | 0.120 | 0.121 |
| P | 25 | 6 | 0.41 | 0.120 | 0.121 |
| P | 40 | 0 | 0.39 | 0.124 | 0.124 |
| P | 40 | 1 | 0.68 | 0.122 | 0.123 |
| P | 40 | 2 | 0.22 | 0.121 | 0.121 |
| P | 40 | 3 | 1.13 | 0.109 | 0.111 |
| P | 40 | 4.5 | 1.60 | 0.116 | 0.118 |
| P | 40 | 6 | 2.70 | 0.110 | 0.113 |
| P | 40 | 6 | 2.72 | 0.110 | 0.113 |

Table 10 shows the concentrations of ESA and adrenalone in the samples at various time points during the study.

TABLE 10

ESA and adrenalone in epinephrine-containing formulations
at various temperatures and time points

| Sample | Condition (° C.) | Time Point (Months) | ESA (%) | Adrenalone (%) |
|---|---|---|---|---|
| A | 25 | 0 | <0.10 | <0.10 |
| A | 25 | 3 | 1.29 | ND |
| A | 25 | 3 | 1.32 | ND |
| A | 25 | 6 | 2.73 | <0.10 |
| A | 25 | 6 | 2.61 | <0.10 |
| A | 40 | 0 | <0.10 | <0.10 |
| A | 40 | 1 | 3.15 | <0.10 |
| A | 40 | 2 | 5.16 | ND |
| A | 40 | 3 | 8.84 | ND |
| A | 40 | 3 | 8.77 | <0.10 |
| A | 40 | 6 | 16.52 | 0.11 |
| A | 40 | 6 | 16.59 | 0.12 |
| B | 25 | 0 | <0.10 | ND |
| B | 25 | 3 | 0.83 | ND |
| B | 25 | 3 | ND | ND |
| B | 25 | 6 | 1.77 | ND |
| B | 25 | 6 | 1.68 | <0.10 |
| B | 40 | 0 | <0.10 | ND |
| B | 40 | 1 | 1.94 | <0.10 |
| B | 40 | 2 | 2.98 | ND |
| B | 40 | 3 | 5.14 | ND |
| B | 40 | 3 | 5.23 | ND |
| B | 40 | 6 | 9.67 | <0.10 |
| B | 40 | 6 | 9.71 | <0.10 |
| C | 25 | 0 | ND | ND |
| C | 40 | 0 | ND | ND |
| C | 40 | 0.9 | 2.24 | ND |
| C | 40 | 2 | 5.05 | <0.10 |
| C | 40 | 3 | 7.88 | ND |
| C | 40 | 6 | 15.98 | ND |
| D | 25 | 0 | ND | ND |
| D | 25 | 0.9 | 0.32 | ND |
| D | 25 | 2 | 0.76 | <0.10 |
| D | 25 | 3 | 1.15 | ND |
| D | 25 | 4.5 | 1.93 | <0.10 |
| D | 25 | 6 | 2.45 | ND |
| D | 40 | 0 | ND | ND |
| D | 40 | 0.9 | 2.43 | ND |
| D | 40 | 2 | 6.21 | 0.10 |
| D | 40 | 3 | 10.05 | ND |
| D | 40 | 4.5 | 13.96 | 0.11 |
| D | 40 | 6 | 22.74 | ND |
| E | 25 | 0 | ND | ND |
| E | 25 | 0.9 | 0.28 | ND |
| E | 25 | 2 | 0.65 | <0.10 |
| E | 25 | 3 | 0.98 | ND |
| E | 25 | 4.5 | 1.56 | <0.10 |
| E | 25 | 6 | 2.07 | <0.10 |
| E | 40 | 0 | ND | ND |
| E | 40 | 0.9 | 2.14 | ND |
| E | 40 | 2 | 5.00 | <0.10 |
| E | 40 | 3 | 7.42 | <0.10 |
| E | 40 | 4.5 | 10.76 | 0.14 |
| E | 40 | 6 | 14.43 | ND |
| F | 25 | 0 | ND | ND |
| F | 25 | 0.9 | 0.13 | ND |
| F | 25 | 2 | 0.67 | <0.10 |
| F | 25 | 3 | ND | ND |
| F | 25 | 4.5 | 1.64 | <0.10 |
| F | 25 | 6 | 2.05 | ND |
| F | 40 | 0 | ND | ND |
| F | 40 | 0.9 | 2.21 | ND |
| F | 40 | 2 | 5.00 | <0.10 |
| F | 40 | 3 | 7.55 | ND |
| F | 40 | 4.5 | 11.06 | <0.10 |
| F | 40 | 6 | 15.02 | ND |
| G | 25 | 0 | ND | ND |
| G | 25 | 0.9 | 0.32 | ND |
| G | 25 | 2 | 0.68 | <0.10 |
| G | 25 | 3 | 1.03 | ND |
| G | 25 | 4.5 | 1.45 | <0.10 |
| G | 25 | 6 | 2.14 | <0.10 |
| G | 40 | 0 | ND | ND |
| G | 40 | 0.9 | 2.20 | ND |
| G | 40 | 2 | 4.97 | <0.10 |
| G | 40 | 3 | 7.33 | ND |
| G | 40 | 4.5 | 10.60 | 0.12 |
| G | 40 | 6 | 14.71 | ND |
| H | 25 | 0 | ND | ND |
| H | 25 | 0.9 | 0.41 | ND |
| H | 25 | 2 | ND | 10.26 |
| H | 25 | 3 | ND | ND |
| H | 25 | 4.5 | ND | ND |
| H | 25 | 6 | ND | ND |
| H | 40 | 0 | ND | ND |
| H | 40 | 0.9 | 0.55 | ND |
| H | 40 | 2 | 0.14 | 6.27 |
| H | 40 | 3 | 0.69 | ND |
| H | 40 | 4.5 | ND | ND |
| H | 40 | 6 | 0.22 | ND |
| I | 25 | 0 | ND | ND |
| I | 25 | 0.9 | ND | ND |
| I | 25 | 2 | ND | ND |
| I | 25 | 3 | ND | ND |
| I | 25 | 4.5 | ND | <0.10 |
| I | 25 | 6 | ND | ND |
| I | 40 | 0 | ND | ND |
| I | 40 | 0.9 | ND | ND |
| I | 40 | 2 | ND | <0.10 |
| I | 40 | 3 | ND | 0.15 |
| I | 40 | 4.5 | ND | ND |
| I | 40 | 6 | ND | ND |
| J | 25 | 0 | ND | ND |
| J | 25 | 0.9 | ND | ND |
| J | 40 | 0 | ND | ND |
| J | 40 | 0.9 | — | — |
| K | 25 | 0 | ND | ND |
| K | 25 | 1 | ND | ND |
| K | 25 | 2 | 0.48 | <0.10 |
| K | 25 | 3 | 0.74 | ND |
| K | 40 | 0 | ND | ND |
| K | 40 | 1 | 1.80 | ND |
| K | 40 | 2 | 3.56 | ND |
| K | 40 | 3 | 5.29 | <0.10 |
| L | 25 | 0 | ND | ND |
| L | 25 | 1 | ND | ND |
| L | 25 | 2 | 0.48 | ND |
| L | 25 | 3 | 0.79 | ND |
| L | 40 | 0 | ND | ND |
| L | 40 | 1 | 1.67 | ND |
| L | 40 | 2 | <0.10 | <0.10 |

TABLE 10-continued

ESA and adrenalone in epinephrine-containing formulations at various temperatures and time points

| Sample | Condition (° C.) | Time Point (Months) | ESA (%) | Adrenalone (%) |
|---|---|---|---|---|
| L | 40 | 3 | 5.32 | ND |
| M | 25 | 0 | ND | ND |
| M | 25 | 1 | 0.38 | <0.10 |
| M | 25 | 2 | 0.69 | <0.10 |
| M | 25 | 3 | 1.15 | ND |
| M | 25 | 4.5 | 1.72 | <0.10 |
| M | 25 | 6 | 2.34 | ND |
| M | 40 | 0 | ND | ND |
| M | 40 | 1 | 2.10 | <0.10 |
| M | 40 | 2 | 5.53 | <0.10 |
| M | 40 | 3 | 8.30 | ND |
| M | 40 | 4.5 | 13.16 | 2.85 |
| M | 40 | 6 | 15.83 | 0.16 |
| N | 25 | 0 | ND | <0.10 |
| N | 25 | 1 | 0.34 | <0.10 |
| N | 25 | 2 | 0.77 | <0.10 |
| N | 25 | 4.5 | 1.67 | <0.10 |
| N | 25 | 6 | 2.28 | ND |
| N | 25 | 6 | 2.35 | ND |
| N | 40 | 0 | ND | <0.10 |
| N | 40 | 1 | 2.15 | <0.10 |
| N | 40 | 2 | 3.46 | <0.10 |
| N | 40 | 3 | 8.41 | ND |
| N | 40 | 4.5 | 12.57 | 0.10 |
| N | 40 | 6 | 16.45 | 0.12 |
| N | 40 | 6 | 16.70 | 0.13 |
| O | 25 | 0 | ND | ND |
| O | 25 | 1 | 0.17 | <0.10 |
| O | 25 | 2 | 0.43 | ND |
| O | 25 | 3 | — | — |
| O | 40 | 0 | ND | ND |
| O | 40 | 1 | 1.14 | ND |
| O | 40 | 2 | 2.44 | <0.10 |
| O | 40 | 3 | — | — |
| P | 25 | 0 | ND | ND |
| P | 25 | 1 | 0.18 | ND |
| P | 25 | 2 | 0.45 | ND |
| P | 25 | 4.5 | 1.03 | ND |
| P | 25 | 6 | 1.48 | ND |
| P | 25 | 6 | 1.48 | ND |
| P | 40 | 0 | ND | ND |
| P | 40 | 1 | 1.31 | <0.10 |
| P | 40 | 2 | 3.29 | <0.10 |
| P | 40 | 3 | 5.04 | ND |
| P | 40 | 4.5 | 7.43 | <0.10 |
| P | 40 | 6 | 9.94 | ND |
| P | 40 | 6 | 9.84 | ND |

Table 11 shows the concentrations of Impurity A, Impurity B, and Unknown C in the samples at various time points during the study.

TABLE 11

Impurity A, Impurity B, and Unknown C in epinephrine-containing formulations at various temperatures and time points

| Sample | Condition (° C.) | Time Point (Months) | Impurity A (%) | Impurity B (%) | Unknown C (%) |
|---|---|---|---|---|---|
| A | 25 | 0 | 0.14 | ND | 0.28 |
| A | 25 | 3 | ND | 0.16 | 0.54 |
| A | 25 | 3 | ND | 0.15 | ND |
| A | 25 | 6 | 0.24 | 0.14 | 0.69 |
| A | 25 | 6 | 0.25 | 0.16 | 0.78 |
| A | 40 | 0 | 0.14 | ND | 0.28 |
| A | 40 | 1 | 0.68 | 0.44 | 1.30 |
| A | 40 | 2 | 0.28 | 0.23 | 0.88 |
| A | 40 | 3 | ND | 0.29 | 1.05 |
| A | 40 | 3 | 0.29 | 0.27 | 1.06 |
| A | 40 | 6 | 0.46 | 0.33 | 1.29 |
| A | 40 | 6 | 0.33 | 0.36 | 1.22 |
| B | 25 | 0 | <0.10 | <0.10 | ND |
| B | 25 | 3 | ND | 0.12 | ND |
| B | 25 | 3 | ND | 0.10 | ND |
| B | 25 | 6 | <0.10 | 0.10 | ND |
| B | 25 | 6 | 0.24 | 0.13 | <0.10 |
| B | 40 | 0 | <0.10 | <0.10 | ND |
| B | 40 | 1 | 0.35 | 0.28 | ND |
| B | 40 | 2 | 0.37 | 0.28 | ND |
| B | 40 | 3 | 0.54 | 0.44 | ND |
| B | 40 | 3 | 0.40 | 0.41 | ND |
| B | 40 | 6 | 0.86 | 0.59 | <0.10 |
| B | 40 | 6 | 0.85 | 0.65 | ND |
| C | 25 | 0 | <0.10 | <0.10 | ND |
| C | 40 | 0 | <0.10 | <0.10 | ND |
| C | 40 | 0.9 | 0.50 | 0.36 | 0.40 |
| C | 40 | 2 | 0.34 | 0.29 | 0.37 |
| C | 40 | 3 | 0.44 | 0.37 | 0.48 |
| C | 40 | 6 | 0.94 | 0.54 | <0.10 |
| D | 25 | 0 | <0.10 | <0.10 | ND |
| D | 25 | 0.9 | 0.45 | 0.32 | 0.25 |
| D | 25 | 2 | 1.17 | 0.86 | 0.24 |
| D | 25 | 3 | 0.74 | 0.60 | ND |
| D | 25 | 4.5 | 1.39 | 1.01 | 0.37 |
| D | 25 | 6 | 2.86 | 2.01 | 0.19 |
| D | 40 | 0 | <0.10 | <0.10 | ND |
| D | 40 | 0.9 | 0.98 | 0.68 | 0.39 |
| D | 40 | 2 | 4.96 | 3.51 | 1.06 |
| D | 40 | 3 | 4.85 | 3.71 | 1.12 |
| D | 40 | 4.5 | 4.87 | 3.63 | 1.01 |
| D | 40 | 6 | 6.09 | 4.87 | 1.21 |
| E | 25 | 0 | <0.10 | <0.10 | ND |
| E | 25 | 0.9 | 0.30 | 0.21 | 0.29 |
| E | 25 | 2 | 0.18 | 0.15 | 0.28 |
| E | 25 | 3 | ND | 0.20 | ND |
| E | 25 | 4.5 | 0.34 | 0.49 | 0.46 |
| E | 25 | 6 | 0.49 | 0.17 | 0.39 |
| E | 40 | 0 | <0.10 | <0.10 | ND |
| E | 40 | 0.9 | 0.58 | 0.43 | 0.55 |
| E | 40 | 2 | 0.63 | 0.48 | 0.64 |
| E | 40 | 3 | 0.82 | 0.97 | 0.76 |
| E | 40 | 4.5 | 1.54 | 1.02 | 1.01 |
| E | 40 | 6 | 2.16 | 1.98 | 1.20 |
| F | 25 | 0 | <0.10 | <0.10 | ND |
| F | 25 | 0.9 | 0.13 | 0.13 | 0.18 |
| F | 25 | 2 | 0.11 | <0.10 | 0.18 |
| F | 25 | 3 | ND | <0.10 | ND |
| F | 25 | 4.5 | 0.16 | <0.10 | 0.20 |
| F | 25 | 6 | 0.33 | 0.17 | 0.13 |
| F | 40 | 0 | <0.10 | <0.10 | ND |
| F | 40 | 0.9 | 0.39 | 0.30 | 0.35 |
| F | 40 | 2 | 0.40 | 0.33 | 0.41 |
| F | 40 | 3 | ND | 0.37 | 0.40 |
| F | 40 | 4.5 | 0.86 | 0.59 | 0.53 |
| F | 40 | 6 | 1.04 | 0.91 | 0.68 |
| G | 25 | 0 | <0.10 | <0.10 | ND |
| G | 25 | 0.9 | 0.33 | 0.23 | 0.26 |
| G | 25 | 2 | 0.14 | 0.13 | 0.20 |
| G | 25 | 3 | ND | 0.17 | ND |
| G | 25 | 4.5 | 0.26 | 0.11 | 0.41 |
| G | 25 | 6 | 0.47 | 0.35 | 0.34 |
| G | 40 | 0 | <0.10 | <0.10 | ND |
| G | 40 | 0.9 | 0.46 | 0.36 | 0.41 |
| G | 40 | 2 | 0.76 | 0.51 | 0.68 |
| G | 40 | 3 | 0.95 | 0.78 | 0.74 |
| G | 40 | 4.5 | 1.57 | 1.10 | 0.89 |
| G | 40 | 6 | 1.76 | 1.56 | 0.91 |
| H | 25 | 0 | ND | ND | ND |
| H | 25 | 0.9 | ND | 13.22 | ND |
| H | 25 | 2 | 0.39 | ND | ND |
| H | 25 | 3 | ND | 52.54 | ND |
| H | 25 | 4.5 | 0.41 | 50.23 | ND |
| H | 25 | 6 | 0.25 | 54.14 | <0.10 |
| H | 40 | 0 | ND | ND | ND |
| H | 40 | 0.9 | <0.10 | 30.78 | ND |

TABLE 11-continued

Impurity A, Impurity B, and Unknown C in epinephrine-containing formulations at various temperatures and time points

| Sample | Condition (° C.) | Time Point (Months) | Impurity A (%) | Impurity B (%) | Unknown C (%) |
|---|---|---|---|---|---|
| H | 40 | 2 | <0.10 | ND | ND |
| H | 40 | 3 | 0.18 | 22.23 | ND |
| H | 40 | 4.5 | 0.63 | 14.70 | ND |
| H | 40 | 6 | <0.10 | 12.01 | ND |
| I | 25 | 0 | ND | ND | ND |
| I | 25 | 0.9 | ND | ND | ND |
| I | 25 | 2 | ND | ND | ND |
| I | 25 | 3 | ND | ND | ND |
| I | 25 | 4.5 | ND | <0.10 | ND |
| I | 25 | 6 | ND | ND | <0.10 |
| I | 40 | 0 | ND | ND | ND |
| I | 40 | 0.9 | ND | ND | ND |
| I | 40 | 2 | ND | ND | ND |
| I | 40 | 3 | ND | <0.10 | ND |
| I | 40 | 4.5 | ND | 0.77 | <0.10 |
| I | 40 | 6 | ND | ND | ND |
| J | 25 | 0 | ND | ND | ND |
| J | 25 | 0.9 | ND | ND | ND |
| J | 40 | 0 | ND | ND | ND |
| J | 40 | 0.9 | — | — | — |
| K | 25 | 0 | ND | ND | ND |
| K | 25 | 1 | ND | 0.13 | ND |
| K | 25 | 2 | ND | ND | ND |
| K | 25 | 3 | 0.31 | 0.24 | <0.10 |
| K | 40 | 0 | ND | ND | ND |
| K | 40 | 1 | 0.26 | 0.23 | ND |
| K | 40 | 2 | 0.44 | 0.24 | ND |
| K | 40 | 3 | 0.57 | 0.47 | ND |
| L | 25 | 0 | ND | ND | ND |
| L | 25 | 1 | ND | 0.11 | ND |
| L | 25 | 2 | 0.11 | <0.10 | <0.10 |
| L | 25 | 3 | 0.14 | <0.10 | <0.10 |
| L | 40 | 0 | ND | ND | ND |
| L | 40 | 1 | ND | 0.27 | ND |
| L | 40 | 2 | 0.62 | 0.55 | ND |
| L | 40 | 3 | 0.71 | 0.56 | ND |
| M | 25 | 0 | ND | <0.10 | 0.12 |
| M | 25 | 1 | 0.15 | 0.12 | 0.35 |
| M | 25 | 2 | 0.60 | 0.41 | 0.95 |
| M | 25 | 3 | 0.50 | 0.37 | 0.45 |
| M | 25 | 4.5 | 0.34 | 0.25 | 0.58 |
| M | 25 | 6 | 0.55 | 0.44 | ND |
| M | 40 | 0 | ND | <0.10 | 0.12 |
| M | 40 | 1 | 0.41 | 0.32 | 0.74 |
| M | 40 | 2 | 0.94 | 0.71 | 1.04 |
| M | 40 | 3 | 1.05 | 0.83 | 1.09 |
| M | 40 | 4.5 | 2.28 | 1.59 | 1.59 |
| M | 40 | 6 | 4.22 | 3.50 | 1.64 |
| N | 25 | 0 | ND | ND | ND |
| N | 25 | 1 | <0.10 | <0.10 | 0.22 |
| N | 25 | 2 | 0.78 | 0.55 | 1.46 |
| N | 25 | 4.5 | 0.13 | 0.11 | 0.54 |
| N | 25 | 6 | ND | 0.18 | 0.57 |
| N | 25 | 6 | ND | 0.14 | 0.69 |
| N | 40 | 0 | ND | ND | ND |
| N | 40 | 1 | 0.36 | 0.26 | 0.80 |
| N | 40 | 2 | 0.47 | 0.34 | ND |
| N | 40 | 3 | 0.42 | 0.31 | 1.18 |
| N | 40 | 4.5 | 0.42 | 0.32 | 1.56 |
| N | 40 | 6 | ND | 0.35 | 1.65 |
| N | 40 | 6 | ND | 0.38 | 1.73 |
| O | 25 | 0 | <0.10 | <0.10 | ND |
| O | 25 | 1 | 0.17 | 0.13 | ND |
| O | 25 | 2 | 0.21 | 0.20 | ND |
| O | 25 | 3 | — | — | — |
| O | 40 | 0 | <0.10 | <0.10 | ND |
| O | 40 | 1 | 0.79 | 0.65 | ND |
| O | 40 | 2 | 1.75 | 1.31 | ND |
| O | 40 | 3 | — | — | — |
| P | 25 | 0 | ND | <0.10 | ND |
| P | 25 | 1 | <0.10 | <0.10 | ND |
| P | 25 | 2 | 0.13 | 0.10 | ND |
| P | 25 | 4.5 | 0.13 | 0.12 | ND |
| P | 25 | 6 | ND | 0.14 | ND |
| P | 25 | 6 | ND | <0.10 | ND |
| P | 40 | 0 | ND | <0.10 | ND |
| P | 40 | 1 | 0.27 | 0.22 | ND |
| P | 40 | 2 | 0.44 | 0.34 | <0.10 |
| P | 40 | 3 | 0.57 | 0.40 | <0.10 |
| P | 40 | 4.5 | 0.73 | 0.57 | ND |
| P | 40 | 6 | 0.84 | 0.67 | ND |
| P | 40 | 6 | 0.89 | 0.70 | ND |

Table 12 shows the concentrations of adrenochrome sulfonate and total impurities in the samples at various time points during the study.

TABLE 12

Adrenochrome sulfonate and total impurities in epinephrine-containing formulations at various temperatures and time points

| Sample | Condition (° C.) | Time Point (Months) | Adrenochrome Sulfonate (%) | Total Impurities (%) |
|---|---|---|---|---|
| A | 25 | 0 | ND | 0.42 |
| A | 25 | 3 | ND | 2.27 |
| A | 25 | 3 | ND | 1.74 |
| A | 25 | 6 | <0.10 | 4.11 |
| A | 25 | 6 | ND | 4.14 |
| A | 40 | 0 | ND | 0.42 |
| A | 40 | 1 | <0.10 | 5.75 |
| A | 40 | 2 | ND | 7.30 |
| A | 40 | 3 | ND | 10.58 |
| A | 40 | 3 | ND | 10.78 |
| A | 40 | 6 | ND | 19.55 |
| A | 40 | 6 | ND | 19.41 |
| B | 25 | 0 | ND | 0.40 |
| B | 25 | 3 | ND | 1.31 |
| B | 25 | 3 | ND | 0.45 |
| B | 25 | 6 | ND | 2.42 |
| B | 25 | 6 | ND | 2.59 |
| B | 40 | 0 | ND | 0.40 |
| B | 40 | 1 | ND | 3.06 |
| B | 40 | 2 | ND | 4.44 |
| B | 40 | 3 | ND | 7.17 |
| B | 40 | 3 | ND | 7.66 |
| B | 40 | 6 | ND | 13.30 |
| B | 40 | 6 | ND | 11.42 |
| C | 25 | 0 | ND | 0.31 |
| C | 40 | 0 | ND | 0.31 |
| C | 40 | 0.9 | ND | 3.91 |
| C | 40 | 2 | ND | 6.63 |
| C | 40 | 3 | ND | 9.59 |
| C | 40 | 6 | ND | 18.14 |
| D | 25 | 0 | ND | 0.31 |
| D | 25 | 0.9 | ND | 2.82 |
| D | 25 | 2 | ND | 3.46 |
| D | 25 | 3 | ND | 2.79 |
| D | 25 | 4.5 | ND | 5.02 |
| D | 25 | 6 | ND | 7.81 |
| D | 40 | 0 | ND | 0.31 |
| D | 40 | 0.9 | 0.26 | 5.57 |
| D | 40 | 2 | ND | 17.56 |
| D | 40 | 3 | ND | 20.87 |
| D | 40 | 4.5 | 0.72 | 27.35 |
| D | 40 | 6 | 0.86 | 41.90 |
| E | 25 | 0 | ND | 0.31 |
| E | 25 | 0.9 | ND | 1.58 |
| E | 25 | 2 | ND | 1.65 |
| E | 25 | 3 | ND | 1.45 |
| E | 25 | 4.5 | ND | 3.16 |
| E | 25 | 6 | ND | 3.63 |
| E | 40 | 0 | ND | 0.31 |
| E | 40 | 0.9 | ND | 4.39 |

TABLE 12-continued

Adrenochrome sulfonate and total impurities in epinephrine-containing formulations at various temperatures and time points

| Sample | Condition (° C.) | Time Point (Months) | Adrenochrome Sulfonate (%) | Total Impurities (%) |
|---|---|---|---|---|
| E | 40 | 2 | ND | 7.65 |
| E | 40 | 3 | ND | 10.41 |
| E | 40 | 4.5 | ND | 14.77 |
| E | 40 | 6 | <0.10 | 20.80 |
| F | 25 | 0 | ND | 0.31 |
| F | 25 | 0.9 | ND | 1.04 |
| F | 25 | 2 | ND | 2.63 |
| F | 25 | 3 | ND | 0.27 |
| F | 25 | 4.5 | ND | 2.31 |
| F | 25 | 6 | ND | 2.93 |
| F | 40 | 0 | ND | 0.31 |
| F | 40 | 0.9 | ND | 3.71 |
| F | 40 | 2 | ND | 6.91 |
| F | 40 | 3 | ND | 8.74 |
| F | 40 | 4.5 | ND | 13.79 |
| F | 40 | 6 | ND | 18.40 |
| G | 25 | 0 | ND | 0.31 |
| G | 25 | 0.9 | ND | 1.57 |
| G | 25 | 2 | ND | 1.61 |
| G | 25 | 3 | ND | 1.46 |
| G | 25 | 4.5 | ND | 2.74 |
| G | 25 | 6 | <0.10 | 3.54 |
| G | 40 | 0 | ND | 0.31 |
| G | 40 | 0.9 | <0.10 | 3.97 |
| G | 40 | 2 | ND | 7.87 |
| G | 40 | 3 | ND | 10.24 |
| G | 40 | 4.5 | ND | 15.17 |
| G | 40 | 6 | ND | 19.74 |
| H | 25 | 0 | ND | 0.79 |
| H | 25 | 0.9 | ND | 52.50 |
| H | 25 | 2 | ND | 65.92 |
| H | 25 | 3 | ND | 108.68 |
| H | 25 | 4.5 | ND | 105.96 |
| H | 25 | 6 | ND | 114.33 |
| H | 40 | 0 | ND | 0.79 |
| H | 40 | 0.9 | ND | 62.20 |
| H | 40 | 2 | ND | 32.07 |
| H | 40 | 3 | ND | 72.91 |
| H | 40 | 4.5 | ND | 75.23 |
| H | 40 | 6 | ND | 89.39 |
| I | 25 | 0 | ND | 0.33 |
| I | 25 | 0.9 | ND | 0.31 |
| I | 25 | 2 | ND | 0.20 |
| I | 25 | 3 | ND | 0.26 |
| I | 25 | 4.5 | ND | 0.36 |
| I | 25 | 6 | ND | 0.92 |
| I | 40 | 0 | ND | 0.33 |
| I | 40 | 0.9 | ND | 1.34 |
| I | 40 | 2 | ND | 0.48 |
| I | 40 | 3 | ND | 0.54 |
| I | 40 | 4.5 | ND | 4.40 |
| I | 40 | 6 | ND | 6.98 |
| J | 25 | 0 | ND | 0.33 |
| J | 25 | 0.9 | ND | 2.12 |
| J | 40 | 0 | ND | 0.33 |
| J | 40 | 0.9 | — | — |
| K | 25 | 0 | ND | 0.29 |
| K | 25 | 1 | ND | 0.44 |
| K | 25 | 2 | ND | 1.27 |
| K | 25 | 3 | ND | 2.27 |
| K | 40 | 0 | ND | 0.29 |
| K | 40 | 1 | ND | 2.76 |
| K | 40 | 2 | <0.10 | 4.59 |
| K | 40 | 3 | ND | 7.68 |
| L | 25 | 0 | ND | 0.29 |
| L | 25 | 1 | ND | 0.54 |
| L | 25 | 2 | ND | 1.35 |
| L | 25 | 3 | <0.10 | 1.96 |
| L | 40 | 0 | ND | 0.29 |
| L | 40 | 1 | ND | 2.39 |
| L | 40 | 2 | ND | 5.04 |
| L | 40 | 3 | <0.10 | 7.07 |
| M | 25 | 0 | ND | 0.51 |
| M | 25 | 1 | ND | 1.49 |
| M | 25 | 2 | ND | 2.81 |
| M | 25 | 3 | ND | 2.95 |
| M | 25 | 4.5 | ND | 3.49 |
| M | 25 | 6 | ND | 3.63 |
| M | 40 | 0 | ND | 0.51 |
| M | 40 | 1 | ND | 4.15 |
| M | 40 | 2 | <0.10 | 8.79 |
| M | 40 | 3 | ND | 12.37 |
| M | 40 | 4.5 | ND | 12.73 |
| M | 40 | 6 | ND | 27.86 |
| N | 25 | 0 | ND | 0.39 |
| N | 25 | 1 | ND | 1.07 |
| N | 25 | 2 | <0.10 | 3.71 |
| N | 25 | 4.5 | ND | 4.37 |
| N | 25 | 6 | ND | 3.31 |
| N | 25 | 6 | ND | 3.46 |
| N | 40 | 0 | ND | 0.39 |
| N | 40 | 1 | ND | 4.13 |
| N | 40 | 2 | ND | 4.87 |
| N | 40 | 3 | ND | 11.34 |
| N | 40 | 4.5 | ND | 16.21 |
| N | 40 | 6 | ND | 19.10 |
| N | 40 | 6 | ND | 19.48 |
| O | 25 | 0 | ND | 0.38 |
| O | 25 | 1 | ND | 0.87 |
| O | 25 | 2 | ND | 1.02 |
| O | 25 | 3 | — | — |
| O | 40 | 0 | ND | 0.38 |
| O | 40 | 1 | ND | 3.62 |
| O | 40 | 2 | <0.10 | 6.55 |
| O | 40 | 3 | — | — |
| P | 25 | 0 | ND | 0.39 |
| P | 25 | 1 | ND | 0.60 |
| P | 25 | 2 | ND | 0.90 |
| P | 25 | 4.5 | ND | 1.83 |
| P | 25 | 6 | ND | 2.03 |
| P | 25 | 6 | ND | 1.89 |
| P | 40 | 0 | ND | 0.39 |
| P | 40 | 1 | ND | 2.60 |
| P | 40 | 2 | ND | 4.29 |
| P | 40 | 3 | ND | 7.14 |
| P | 40 | 4.5 | ND | 11.22 |
| P | 40 | 6 | ND | 14.15 |
| P | 40 | 6 | ND | 14.15 |

What is claimed is:

1. A composition comprising:
   in the range of about 0.75 to 1.25 mg/mL of epinephrine and/or salts thereof,
   in the range of about 6 to 8 mg/mL of a tonicity regulating agent,
   in the range of 2 and 15 mg/mL of tartaric acid,
   in the range of 1 and 5 mg/mL of sodium hydroxide,
   in the range of about 0.4 and 0.5 mg/mL of an antioxidant,
   in the range of about 0.001 to 0.010 mL/mL of a pH lowering agent,
   wherein the antioxidant comprises sodium bisulfite and/or sodium metabisulfite, and
   wherein the composition comprises about 3% or less total impurities after 6 months of storage at between 23° C. and 32° C. and between 55% RH and 70% RH.

2. The composition of claim 1, wherein the tonicity regulating agent comprises sodium chloride.

3. The composition of claim 1, wherein the pH lowering agent comprises hydrochloric acid.

4. The composition of claim 1, further comprising a solvent.

* * * * *